(12) United States Patent
Rzadkiewicz et al.

(10) Patent No.: US 8,117,048 B1
(45) Date of Patent: Feb. 14, 2012

(54) ELECTRONIC HEALTH RECORD SYSTEM AND METHOD FOR AN UNDERSERVED POPULATION

(75) Inventors: Mary Johnice Rzadkiewicz, Buffalo, NY (US); Janet M. Stoeckl, Amherst, NY (US); Roberta Rifkin, Williamsville, NY (US); Ryan William Brown, Orchard Park, NY (US); Justin Michael Del Vecchio, Cheektowaga, NY (US); Alex James, Clarence Center, NY (US); Lauren Schmidt, Youngstown, NY (US); Michael Nusinov, Getzville, NY (US)

(73) Assignees: Independent Health Association, Inc., Buffalo, NY (US); CUBRC, Buffalo, NY (US)

(*) Notice: Subject to any disclaimer, the term of this patent is extended or adjusted under 35 U.S.C. 154(b) by 390 days.

(21) Appl. No.: 12/290,475

(22) Filed: Oct. 31, 2008

(51) Int. Cl.
G06F 19/00 (2011.01)
(52) U.S. Cl. .................. 705/3; 600/300; 710/73
(58) Field of Classification Search ............ 705/3; 1/1; 600/300; 710/73
See application file for complete search history.

(56) References Cited

U.S. PATENT DOCUMENTS

| | | | |
|---|---|---|---|
| 3,571,947 A | 3/1971 | Maddison et al. | |
| 5,169,342 A | 12/1992 | Steele et al. | |
| 5,720,502 A | 2/1998 | Cain | |
| 5,772,585 A * | 6/1998 | Lavin et al. | 600/300 |
| 6,085,752 A | 7/2000 | Kehr et al. | |
| 6,314,405 B1 | 11/2001 | Richardson | |
| 6,383,135 B1 | 5/2002 | Chikovani et al. | |
| 6,422,875 B1 | 7/2002 | Patak et al. | |
| 6,684,276 B2 * | 1/2004 | Walker et al. | 710/73 |
| 6,804,656 B1 * | 10/2004 | Rosenfeld et al. | 705/3 |
| 7,107,547 B2 | 9/2006 | Cule et al. | |
| 2004/0088317 A1 * | 5/2004 | Fabrick et al. | 707/102 |
| 2004/0138924 A1 | 7/2004 | Pristine | |
| 2005/0039127 A1 | 2/2005 | Davis | |
| 2005/0089823 A1 | 4/2005 | Stillman | |
| 2007/0094197 A1 | 4/2007 | Datena et al. | |
| 2007/0294113 A1 * | 12/2007 | Settimi | 705/3 |

OTHER PUBLICATIONS

Dyan R. Blewitt, MS, G. Octo Barnett M.D., Henry C. Chueh, M.D., M.S., Laboratory of Computer Science, Massachusetts General Hospital, Boston, MA, 1999, AMIA.*
Dialog search history.*

* cited by examiner

Primary Examiner — Dilek B Cobanoglu
(74) Attorney, Agent, or Firm — Simpson & Simpson, PLLC

(57) ABSTRACT

A system for managing electronic health records, including: an interface element in at least one specially programmed general-purpose computer for receiving data regarding at least one environmental condition, at least one symptom related to physical or mental health, and background for the patient; a memory element for the computer for storing the data; and a processor in the computer for: generating, using the data, information regarding at least one concern with respect to the physical or mental health of the patient; and generating, using the data, at least one action item for addressing the at least one concern. The interface element is for transmitting at least a portion of the information regarding the at least one concern for the physical or mental health of the patient and the at least one action item for display and receiving data regarding compliance with the at least one action item.

12 Claims, 22 Drawing Sheets

ELECTRONIC HEALTH RECORD SYSTEM AND METHOD FOR AN UNDERSERVED POPULATION

REFERENCE TO COMPUTER PROGRAM LISTING APPENDIX

The present application includes a computer program listing appendix on compact disc. Two duplicate compact discs are provided herewith. Each compact disc contains an ASCII text file of the computer program listing as follows:

| Size (bytes) | File Name | Last Updated |
|---|---|---|
| DIR | ./ | |
| 1,899 | YPOH.sln | Mar. 27, 2007 |
| DIR | ./Client | |
| 3,352 | app.config | May 27, 2007 |
| 563 | App.xaml | Apr. 25, 2007 |
| 342 | App.xaml.cs | Apr. 25, 2007 |
| 32,755 | Client.csproj | May 3, 2007 |
| 330 | CustomEnums.cs | Jul. 16, 2008 |
| 19,660 | DataConverters.cs | Apr. 26, 2007 |
| 1,371 | GenericConcern.cs | Jul. 16, 2008 |
| 735 | Host.xaml | Jul. 16, 2008 |
| 2,603 | Host.xaml.cs | Jul. 16, 2008 |
| 184 | ICommitable.cs | Apr. 25, 2007 |
| 228 | IConcern.cs | Jun. 1, 2007 |
| 19,042 | Login.xaml | Jun. 12, 2007 |
| 9,993 | Login.xaml.cs | Jun. 12, 2007 |
| 8,898 | Main.xaml | May 3, 2007 |
| 11,315 | Main.xaml.cs | May 3, 2007 |
| 9,213 | Resources.xaml | Apr. 27, 2007 |
| 56,144 | SessionData.cs | Apr. 27, 2007 |
| 574 | Settings.cs | Jun. 18, 2007 |
| 798 | USStates.cs | May 8, 2007 |
| DIR | ./Client/Content | |
| 10,926 | Developing.xaml | Jun. 12, 2007 |
| 2,699 | Developing.xaml.cs | Jun. 12, 2007 |
| 15,230 | DevelopingEnvironment.xaml | Jun. 12, 2007 |
| 16,123 | DevelopingEnvironment.xaml.cs | Jun. 12, 2007 |
| 20,365 | DevelopingFamily.xaml | Jun. 18, 2007 |
| 10,717 | DevelopingFamily.xaml.cs | Jun. 18, 2007 |
| 9,986 | DevelopingMedications.xaml | Jun. 12, 2007 |
| 8,968 | DevelopingMedications.xaml.cs | Jun. 12, 2007 |
| 19,987 | DevelopingMental.xaml | Jun. 1, 2007 |
| 21,037 | DevelopingMental.xaml.cs | Jun. 1, 2007 |
| 12,953 | DevelopingPhysical.xaml | Jun. 12, 2007 |
| 19,369 | DevelopingPhysical.xaml.cs | Jun. 12, 2007 |
| 5,436 | HealthAlbum.xaml | Apr. 25, 2007 |
| 26,201 | HealthAlbum.xaml.cs | Apr. 25, 2007 |
| 9,526 | HTSH.xaml | Jul. 16, 2008 |
| 4,154 | HTSH.xaml.cs | Jul. 16, 2008 |
| 35,969 | Snapshot.xaml | May 1, 2007 |
| 24,840 | Snapshot.xaml.cs | May 1, 2007 |
| DIR | ./Client/Content/Album | |
| 7,852 | IndexCard.xaml | Jun. 12, 2007 |
| 8,181 | IndexCard.xaml.cs | Jun. 12, 2007 |
| DIR | ./Client/Content/Mental | |
| 24,539 | Abuse.xaml | Jun. 1, 2007 |
| 6,831 | Abuse.xaml.cs | Jun. 1, 2007 |
| 14,256 | AlcoholScreening.xaml | Jun. 1, 2007 |
| 7,409 | AlcoholScreening.xaml.cs | Jun. 1, 2007 |
| 6,618 | CAGE.xaml | Jun. 1, 2007 |
| 3,008 | CAGE.xaml.cs | Jun. 1, 2007 |
| 20,023 | PHQ9.xaml | Jun. 1, 2007 |
| 6,265 | PHQ9.xaml.cs | Jun. 1, 2007 |
| DIR | ./Client/Controls | |
| 2,564 | AccessKeyScoper.cs | Jun. 8, 2007 |
| 2,531 | Education.xaml | May 11, 2007 |
| 1,494 | Education.xaml.cs | May 11, 2007 |
| 2,606 | WebBrowserControl.cs | Jun. 8, 2007 |
| 1,987 | WebBrowserControl.designer.cs | Jun. 8, 2007 |
| 380 | WebCam.xaml | Jun. 8, 2007 |
| 3,112 | WebCam.xaml.cs | Jun. 8, 2007 |
| DIR | ./Client/Properties | |

-continued

| Size (bytes) | File Name | Last Updated |
|---|---|---|
| 2,286 | AssemblyInfo.cs | Apr. 25, 2007 |
| 3,923 | Resources.Designer.cs | May 11, 2007 |
| 1,091 | Settings.Designer.cs | Jun. 9, 2007 |
| DIR | ./Client/Service References/Service.ClientSearch | |
| 666 | Client.Service.ClientSearch.ClientSearchObject.datasource | Jun. 8, 2007 |
| 387 | ClientSearch.disco | Jun. 8, 2007 |
| 3,363 | ClientSearch.wsdl | Jun. 8, 2007 |
| 914 | ClientSearch.xsd | Jun. 8, 2007 |
| 2,398 | ClientSearch1.xsd | Jun. 8, 2007 |
| 1,028 | ClientSearch2.xsd | Jun. 8, 2007 |
| 2,331 | configuration.svcinfo | Jun. 8, 2007 |
| 5,767 | Reference.cs | Jun. 8, 2007 |
| 2,451 | Reference.svcmap | Jun. 8, 2007 |
| DIR | ./Client/Service References/Service.Education | |
| 654 | Client.Service.Education.EducationObject.datasource | Jun. 8, 2007 |
| 2,283 | configuration.svcinfo | Jun. 8, 2007 |
| 381 | Education.disco | Jun. 8, 2007 |
| 5,466 | Education.wsdl | Jun. 8, 2007 |
| 1,231 | Education.xsd | Jun. 8, 2007 |
| 1,953 | Education1.xsd | Jun. 8, 2007 |
| 2,398 | Education2.xsd | Jun. 8, 2007 |
| 8,404 | Reference.cs | Jun. 8, 2007 |
| 2,418 | Reference.svcmap | Jun. 8, 2007 |
| DIR | ./Client/Service References/Service.Main | |
| 632 | Client.Service.Main.BMIObject.datasource | Jun. 8, 2007 |
| 640 | Client.Service.Main.ConcernObject.datasource | Jun. 8, 2007 |
| 652 | Client.Service.Main.DevelopFamilyObject.datasource | Jun. 8, 2007 |
| 648 | Client.Service.Main.EnvironmentObject.datasource | Jun. 8, 2007 |
| 654 | Client.Service.Main.PhysicalHealthObject.datasource | Jun. 8, 2007 |
| 650 | Client.Service.Main.PrescriptionObject.datasource | Jun. 8, 2007 |
| 650 | Client.Service.Main.UserSnapshotObject.datasource | Jun. 8, 2007 |
| 2,206 | configuration.svcinfo | Jun. 8, 2007 |
| 371 | Main.disco | Jun. 8, 2007 |
| 31,727 | Main.wsdl | Jun. 8, 2007 |
| 15,435 | Main.xsd | Jun. 8, 2007 |
| 2,398 | Main1.xsd | Jun. 8, 2007 |
| 31,130 | Main2.xsd | Jun. 8, 2007 |
| 1,382 | Main3.xsd | Jun. 8, 2007 |
| 181,732 | Reference.cs | Jun. 8, 2007 |
| 2,544 | Reference.svcmap | Jun. 8, 2007 |
| DIR | ./Client/Service References/Service.Photo | |
| 2,219 | configuration.svcinfo | Jun. 8, 2007 |
| 373 | Photo.disco | Jun. 8, 2007 |
| 4,103 | Photo.wsdl | Jun. 8, 2007 |
| 2,398 | Photo.xsd | Jun. 8, 2007 |
| 1,017 | Photo1.xsd | Jun. 8, 2007 |
| 1,383 | Photo2.xsd | Jun. 8, 2007 |
| 2,666 | Reference.cs | Jun. 8, 2007 |
| 2,374 | Reference.svcmap | Jun. 8, 2007 |
| DIR | ./Client/Service References/Services.Prevention | |
| 658 | Client.Service.Prevention.PreventionObject.datasource | Jun. 8, 2007 |
| 2,299 | configuration.svcinfo | Jun. 8, 2007 |
| 383 | Prevention.disco | Jun. 8, 2007 |
| 5,534 | Prevention.wsdl | Jun. 8, 2007 |
| 2,398 | Prevention.xsd | Jun. 8, 2007 |
| 2,036 | Prevention1.xsd | Jun. 8, 2007 |
| 2,265 | Prevention2.xsd | Jun. 8, 2007 |
| 10,590 | Reference.cs | Jun. 8, 2007 |
| 2,429 | Reference.svcmap | Jun. 8, 2007 |
| DIR | ./Client/Service References/Service.StaffLogin | |
| 658 | Client.Service.StaffLogin.StaffLoginObject.datasource | Jun. 8, 2007 |
| 2,299 | configuration.svcinfo | Jun. 8, 2007 |
| 6,192 | Reference.cs | Jun. 8, 2007 |
| 2,429 | Reference.svcmap | Jun. 8, 2007 |
| 383 | StaffLogin.disco | Jun. 8, 2007 |
| 3,255 | StaffLogin.wsdl | Jun. 8, 2007 |
| 970 | StaffLogin.xsd | Jun. 8, 2007 |
| 2,398 | StaffLogin1.xsd | Jun. 8, 2007 |

-continued

| Size (bytes) | File Name | Last Updated |
|---|---|---|
| 763 | StaffLogin2.xsd | Jun. 8, 2007 |
| DIR | ./Server | |
| 3,414 | App.config | |
| 113 | ClientSearch.svc | Jun. 8, 2007 |
| 4,179 | ClientSearch.svc.cs | Jun. 8, 2007 |
| 23,639 | Concern.cs | Jun. 8, 2007 |
| 42,185 | DevelopEnvironment.cs | Jun. 8, 2007 |
| 39,392 | DevelopFamily.cs | Jun. 8, 2007 |
| 4,820 | DevelopMain.cs | Jun. 8, 2007 |
| 43,998 | DevelopMentalHealth.cs | Jun. 8, 2007 |
| 17,840 | DevelopPhysicalHealth.cs | Jun. 8, 2007 |
| 33,499 | DevelopPrescriptions.cs | Jun. 8, 2007 |
| 107 | Education.svc | Jun. 8, 2007 |
| 11,786 | Education.svc.cs | Jun. 8, 2007 |
| 356 | IClientSearch.cs | Jun. 8, 2007 |
| 545 | IEducation.cs | Jun. 8, 2007 |
| 395 | IMain.cs | Jun. 8, 2007 |
| 411 | IPhoto.cs | Jun. 8, 2007 |
| 564 | IPrevention.cs | Jun. 8, 2007 |
| 355 | IStaffLogin.cs | Jun. 8, 2007 |
| 1,341 | Log.cs | Jul. 16, 2008 |
| 97 | Main.svc | Jun. 8, 2007 |
| 12,520 | Main.svc.cs | Jun. 8, 2007 |
| 99 | Photo.svc | Jun. 8, 2007 |
| 2,585 | Photo.svc.cs | Jun. 8, 2007 |
| 109 | Prevention.svc | Jun. 8, 2007 |
| 18,532 | Prevention.svc.cs | Jun. 8, 2007 |
| 1,158 | Program.cs | Jun. 8, 2007 |
| 7,123 | Server.csproj | Jun. 8, 2007 |
| 1,387 | Settings.cs | Jun. 8, 2007 |
| 109 | StaffLogin.svc | Jun. 8, 2007 |
| 3,168 | StaffLogin.svc.cs | Jun. 8, 2007 |
| 58,339 | UserSnapshot.cs | Jun. 8, 2007 |
| 3,161 | Web.config | Jun. 8, 2007 |
| 2,182 | YPOHServiceHost.cs | Jun. 8, 2007 |
| DIR | ./Server/Data | |
| 12,907 | Database.cs | Jun. 8, 2007 |
| 612 | Format.cs | Jun. 8, 2007 |
| 888 | ParamObject.cs | Jun. 8, 2007 |
| DIR | ./Server/Properties | |
| 1,393 | AssemblyInfo.cs | Jun. 8, 2007 |
| DIR | ./Old | |
| 6,697 | PictureOfHealth.mxml | Dec. 1, 2006 |
| 981 | StringMatchingChecker.mxml | Dec. 1, 2006 |
| DIR | ./Old/myComponent | |
| 2,481 | AddMemberPopup.mxml | Nov. 17, 2006 |
| 2,016 | AddNewClient.mxml | Nov. 17, 2006 |
| 11,075 | BasicInfo.mxml | Oct. 10, 2006 |
| 15,501 | Copy of Sidebar.mxml | Nov. 17, 2006 |
| 860 | CreateNew.mxml | Oct. 10, 2006 |
| 32,506 | DevelopingScreen.mxml | Dec. 1, 2006 |
| 19,417 | DevelopingSubScreen.mxml | Nov. 28, 2006 |
| 1,763 | LoginBox.mxml | Dec. 1, 2006 |
| 2,444 | PantryVoucher.mxml | Oct. 10, 2006 |
| 18,883 | Sidebar.mxml | Nov. 28, 2006 |
| 7,468 | SnapshotScreen.mxml | Dec. 1, 2006 |
| DIR | ./Old/PHPScript | |
| 1,122 | addClient.php | Nov. 28, 2006 |
| 814 | addDevelopingInfo.php | Nov. 28, 2006 |
| 0 | getClientInfo.php | Nov. 28, 2006 |
| 787 | getClients.php | Nov. 28, 2006 |
| 879 | getClientSnapshotInfo.php | Nov. 28, 2006 |
| 854 | login.php | Nov. 28, 2006 |
| 1,039 | photoUpload.php | Nov. 28, 2006 |
| 904 | updateClientDevelopingInfo.php | Nov. 28, 2006 |
| 883 | updateClientSnapshotInfo.php | Nov. 28, 2006 |
| 1,075 | writeuser.php | Nov. 28, 2006 |
| DIR | ./Old/PoHScripts | |
| 5,742 | Handlers.as | Dec. 1, 2006 |
| 5,712 | SnapshotHandlers.as | Dec. 1, 2006 |
| 1,056 | StringHelper.as | Nov. 17, 2006 |
| 2,281 | StringMatcher.as | Dec. 1, 2006 |

The computer program listing appendix is hereby expressly incorporated by reference in the present application.

FIELD OF THE INVENTION

The invention relates generally to a system and method for generating, managing, and monitoring electronic health records, in particular, for an underserved population. More specifically, the present invention addresses personal and environmental factors affecting health and uses an easy to understand graphical format for presenting and gathering information.

BACKGROUND OF THE INVENTION

Systems for eliciting information from patients regarding physical symptoms are known. It would be desirable to expand the scope and nature of information obtained from patients regarding factors affecting health of the patients.

SUMMARY OF THE INVENTION

The invention broadly comprises a system for managing electronic health records, including: an interface element in at least one specially programmed general-purpose computer for receiving first data regarding at least one environmental condition related to a patient, second data regarding at least one symptom of the patient related to physical or mental health of the patient, and background data for the patient; a memory element for the at least one specially programmed general-purpose computer for storing the first, second, and background data; and a processor in the at least one specially programmed general-purpose computer for: generating, using the first, second, and background data, information regarding at least one concern applicable to the physical or mental health of the patient; and generating, using the first, second, and background data, at least one action item for addressing the at least one concern. The interface element is for transmitting at least a portion of the information regarding the at least one concern for the physical or mental health of the patient and the at least one action item for display and receiving third data regarding compliance with the at least one action item.

In one embodiment, the at least one action item includes an action item directed to an environmental condition from the at least one environmental condition; the processor is for generating a graphical presentation including at least one inquiry, in the form of a pictorial display, regarding compliance of the patient with the action item directed to an environmental condition; and the interface element is for transmitting the graphical presentation for display on a graphical user interface (GUI) and receiving data regarding compliance of the patient with the action item directed to an environmental condition via a GUI on which the graphical presentation is displayed.

In another embodiment, the processor is for generating a graphical presentation including a plurality of inquiries, in the form of respective pictorial displays, regarding a plurality of respective environmental conditions; and the interface element is for transmitting the graphical presentation for display on a GUI and receiving at least a portion of the first data via a GUI on which the graphical presentation is displayed. In a further embodiment, the at least one environmental condition is selected from the group consisting of whether the patient is homeless, the type of residence in which the patient lives, conditions in the vicinity of the patient's residence, utilities for and infrastructure of the patient's residence, household items associated with the patient's residence, personal items belonging to the patient, transportation options available to the patient, and personal safety issues.

In one embodiment, the at least one action item addresses an environmental condition from the at least one environmental condition. In another embodiment, the processor is for generating an inquiry as to whether the patient wishes further information regarding the at least one health concern; the interface element is for transmitting the inquiry for display and receiving an affirmative response to the inquiry, including a request for further information regarding a health concern from the at least one health concern; the processor is for generating information regarding the health concern, the information regarding the health concern more detailed than the information regarding the at least one concern for the physical or mental health of the patient; and the interface element is for transmitting the information regarding the health concern.

The invention further broadly comprises a method for managing electronic health care records.

It is a general object of the present invention to provide a system and a method for generating, managing, and monitoring electronic health records, in particular, for an underserved population. More specifically, the present invention is intended to addresses personal and environmental factors affecting health and uses an easy to understand graphical format for presenting and gathering information.

These and other objects and advantages of the present invention will be readily appreciable from the following description of preferred embodiments of the invention and from the accompanying drawings and claims.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein shall include the same meaning as commonly understood to one of ordinary skill in the art to which this invention belongs. Although any methods, devices or materials similar or equivalent to those described herein can be used in the practice or testing of the invention, the preferred methods, devices, and materials are now described.

It should be understood that the use of "or" in the present application is with respect to a "non-exclusive" arrangement, unless stated otherwise. For example, when saying that "item x is A or B," it is understood that this can mean one of the following: 1) item x is only one or the other of A and B; and 2) item x is both A and B. Alternately stated, the word "or" is not used to define an "exclusive or" arrangement. For example, an "exclusive or" arrangement for the statement "item x is A or B" would require that x can be only one of A and B.

Figure 1:
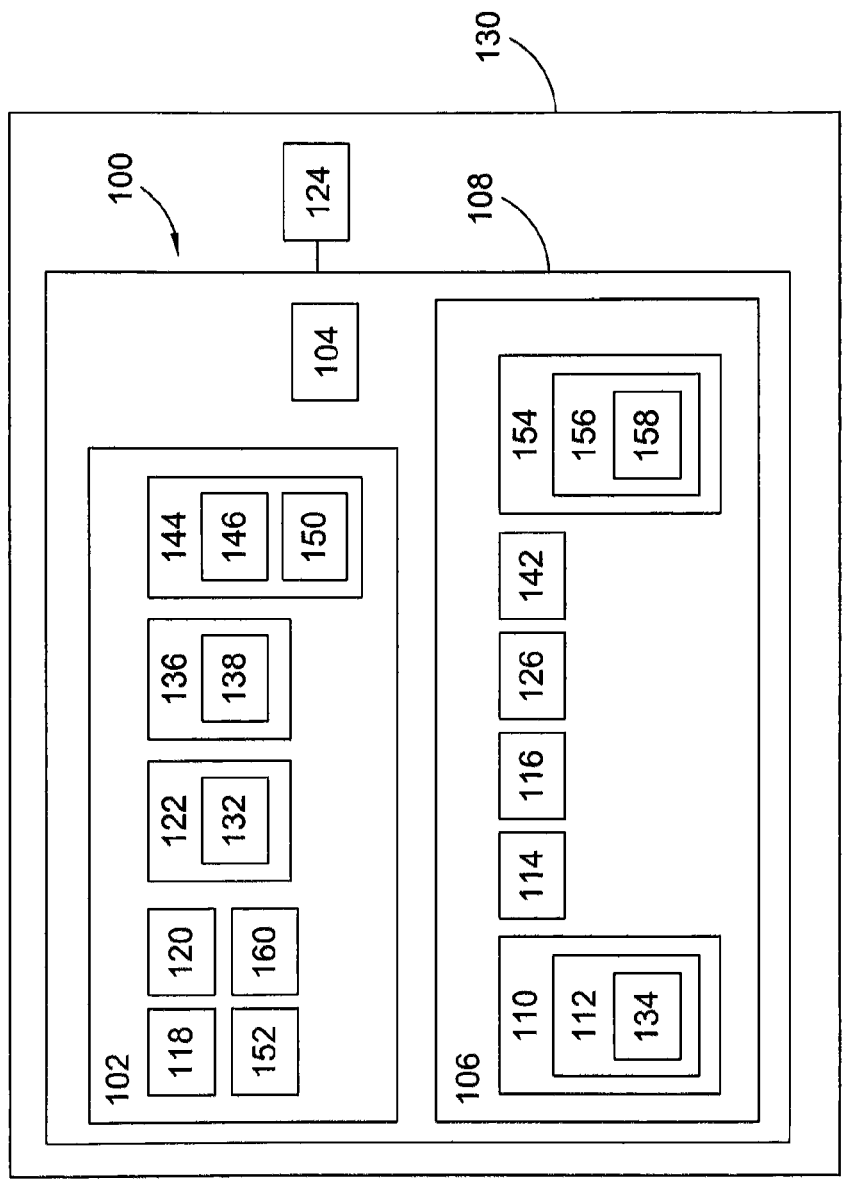
FIG. 1 is a schematic block diagram of a present invention system for managing electronic health records.

FIG. 1 is a block diagram for present invention system 100 for managing electronic health records. System 100 includes: processor 102, interface element 104, and memory element, or unit, 106 of at least one specially programmed general-purpose computer 108. The interface element is for receiving data 110 regarding at least one environmental condition 112 related to a patient (not shown), data 114 regarding at least one symptom of the patient related to physical or mental health of the patient, and background data 116 for the patient. The memory element stores data 110, 114, and 116.

The processor is for generating, using data 110, 114, and 116, information 118 regarding at least one concern 120 applicable to the physical or mental health of the patient. For example, using data 110, 114, and 116, the processor identifies concern 120 and then generates information 118, which is descriptive of the health concern. It should be understood that the concern may be directly related to the patient, for example, a physical or mental symptom or condition, or can be directed to a situation or condition in which the patient finds them self or that otherwise impacts the patient's well-being, as further described infra. The processor also generates, using data 110, 114, and 116, at least one action item 122 for addressing the at least one concern. The interface element is for transmitting at least a portion of information 118 and action item 122 for display, for example, on graphical user interface (GUI) 124, and receiving data 126 regarding compliance with the at least one action item, for example, from GUI 124. Data 126 is stored in the memory element. The patient can directly input data 126 in the system in response to pictorial or graphic displays on the GUI or a health care provider can obtain the information from the patient and input the information.

By interface element, we mean any combination of hardware, firmware, or software in a computer used to enable communication or data transfer between the computer and a device, system, or network external to the computer. The interface element can connect with the device, system, or network external to the computer, for example, GUI 124, using any means known in the art, including, but not limited to a hardwire connection, an optical connection, an Internet connection, or a radio frequency connection. Processor 102, interface element 104, and memory element 106 can be any processor, interface element, or memory element, respectively, or combination thereof, known in the art.

Computer 108 can be any computer or plurality of computers known in the art. In one embodiment, the computer is located in a health care location with which system 100 is associated, for example, location 130. In another embodiment (not shown), all or parts of the computer are remote from retail locations with which system 100 is associated. In a further embodiment, computer 108 is associated with a plurality of health care locations with which system 100 is associated. Thus, the computer provides the functionality described supra and infra for more than one health care location.

In one embodiment, the at least one action item includes action item 132 directed to environmental condition 134 from the at least one environmental condition; the processor is for generating graphical presentation 136 including at least one inquiry 138, including a pictorial display, regarding compliance of the patient with action item 132; and, the interface element is for transmitting the graphical presentation for display on a GUI, for example, GUI 124, and receiving data 142 regarding compliance of the patient with action item 132, for example, as displayed via a GUI 124. Data 142 is stored in the memory element.

In another embodiment, the processor is for generating graphical presentation 144 including a plurality of inquiries 146, including respective pictorial displays, regarding a plurality of respective environmental conditions 150; and the interface element is for transmitting graphical presentation 144 for display on a GUI, for example, GUI 124, and receiving at least a portion of data 110 via a GUI on which the graphical presentation is displayed, for example, GUI 124. That is, condition 112 is selected from conditions 150.

In one embodiment, environmental conditions 150 include, but are not limited to whether the patient is homeless, the type of residence in which the patient lives, conditions in the vicinity of the patient's residence, utilities for and infrastructure of the patient's residence, household items associated with the patient's residence, personal items belonging to the patient, transportation options available to the patient, and personal safety issues.

In another embodiment, the processor is for generating inquiry 152 as to whether the patient wishes further information regarding the at least one health concern and the interface element is for transmitting the inquiry for display, for example, on GUI 124, and receiving affirmative response 154, for example, via GUI 124, to the inquiry. The affirmative response includes request 156 for further information regarding health concern 158 from health concerns 120. Response 154 is stored in the memory element. The processor generates information 160 regarding health concern 158, information 160 more detailed than information 118. The interface element transmits information 160, for display, for example, on GUI 124.

It should be understood that various storage and removal operations, not explicitly described above, involving memory 106 and as known in the art, are possible with respect to the operation of system 100. For example, outputs from and inputs to the general-purpose computer can be stored and retrieved from the memory elements and data generated by the processor can be stored in and retrieved from the memory.

Figure 2:
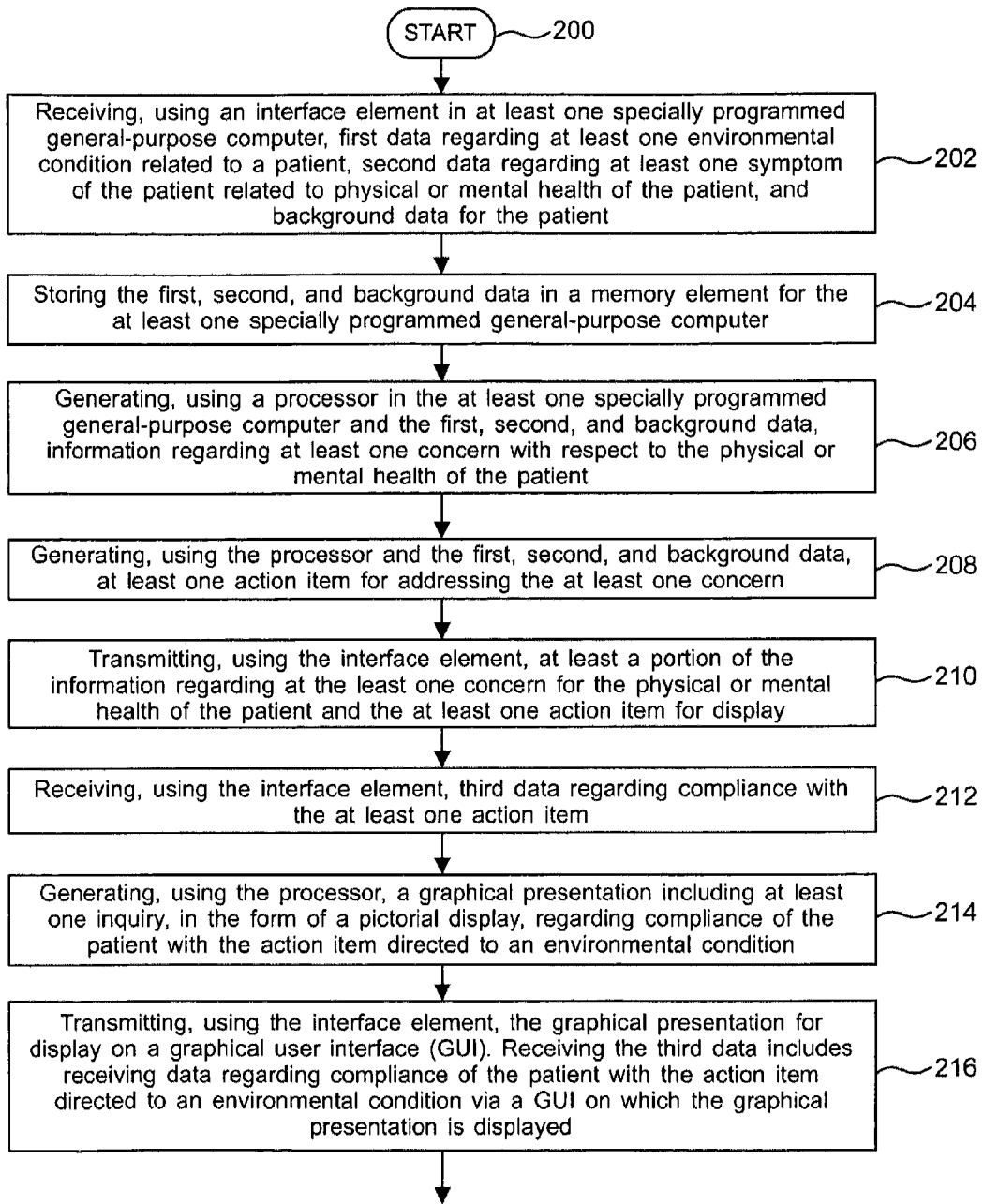
FIG. 2 is a flow chart of a present invention method for managing electronic health records; and, FIGS. 3-21 include screen captures illustrating a present invention system and method.
Figure 2:
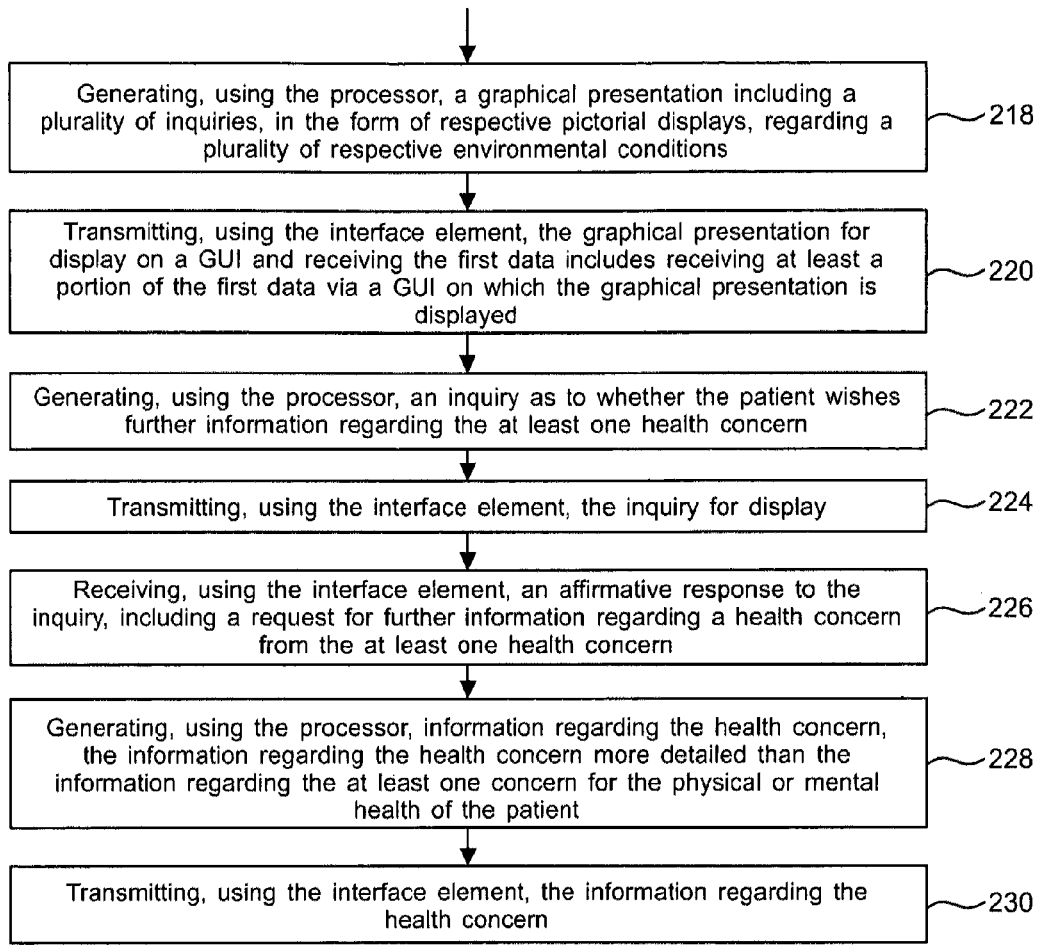

FIG. 2 is a flow chart illustrating a present invention computer-based method for managing electronic health records. Although the method in FIG. 2 is depicted as a sequence of numbered steps for clarity, no order should be inferred from the numbering unless explicitly stated. The method starts at Step 200. Step 202 receives, using an interface element in at least one specially programmed general-purpose computer, first data regarding at least one environmental condition related to a patient, second data regarding at least one symptom of the patient related to physical or mental health of the patient, and background data for the patient; step 204 stores the first, second, and background data in a memory element for the at least one specially programmed general-purpose computer; step 206 generates, using a processor in the at least one specially programmed general-purpose computer and the first, second, and background data, information applicable to at least one concern with respect to the physical or mental health of the patient; step 208 generates, using the processor and the first, second, and background data, at least one action item for addressing the at least one concern; step 210 transmits, using the interface element, at least a portion of the information regarding at least one concern for the physical or mental health of the patient and the at least one action item for display; and step 212 receives, using the interface element, third data regarding compliance with the at least one action item.

In one embodiment, the at least one action item includes an action item directed to an environmental condition from the at least one environmental condition, step 214, generates, using the processor, a graphical presentation including at least one inquiry, including a pictorial display, regarding compliance of the patient with the action item directed to an environmental condition; and step 216 transmits, using the interface element, the graphical presentation for display on a graphical user interface (GUI). Receiving the third data includes receiving data regarding compliance of the patient with the action item directed to an environmental condition via a GUI on which the graphical presentation is displayed.

In another embodiment, step 218 generates, using the processor, a graphical presentation including a plurality of inquiries, with respective pictorial displays, regarding a plurality of respective environmental conditions; and step 220 transmits, using the interface element, the graphical presentation for display on a GUI. Then, receiving the first data includes receiving at least a portion of the first data via a GUI on which the graphical presentation is displayed.

In a further embodiment, the at least one environmental condition includes whether the patient is homeless, the type of residence in which the patient lives, conditions in the vicinity of the patient's residence, utilities for and infrastructure of the patient's residence, household items associated with the patient's residence, personal items belonging to the patient, transportation options available to the patient, and personal safety issues.

In one embodiment, the at least one action item addresses an environmental condition from the at least one environmental condition. In another embodiment, step 222 generates, using the processor, an inquiry as to whether the patient wishes further information regarding the at least one health concern; step 224 transmits, using the interface element, the inquiry for display; step 226 receives, using the interface element, an affirmative response to the inquiry, including a request for further information regarding a health concern from the at least one health concern; step 228 generates, using the processor, information regarding the health concern, the information regarding the health concern more detailed than the information regarding at least one concern for the physical or mental health of the patient; and step 230 transmits, using the interface element, the information regarding the health concern.

Figure 3:
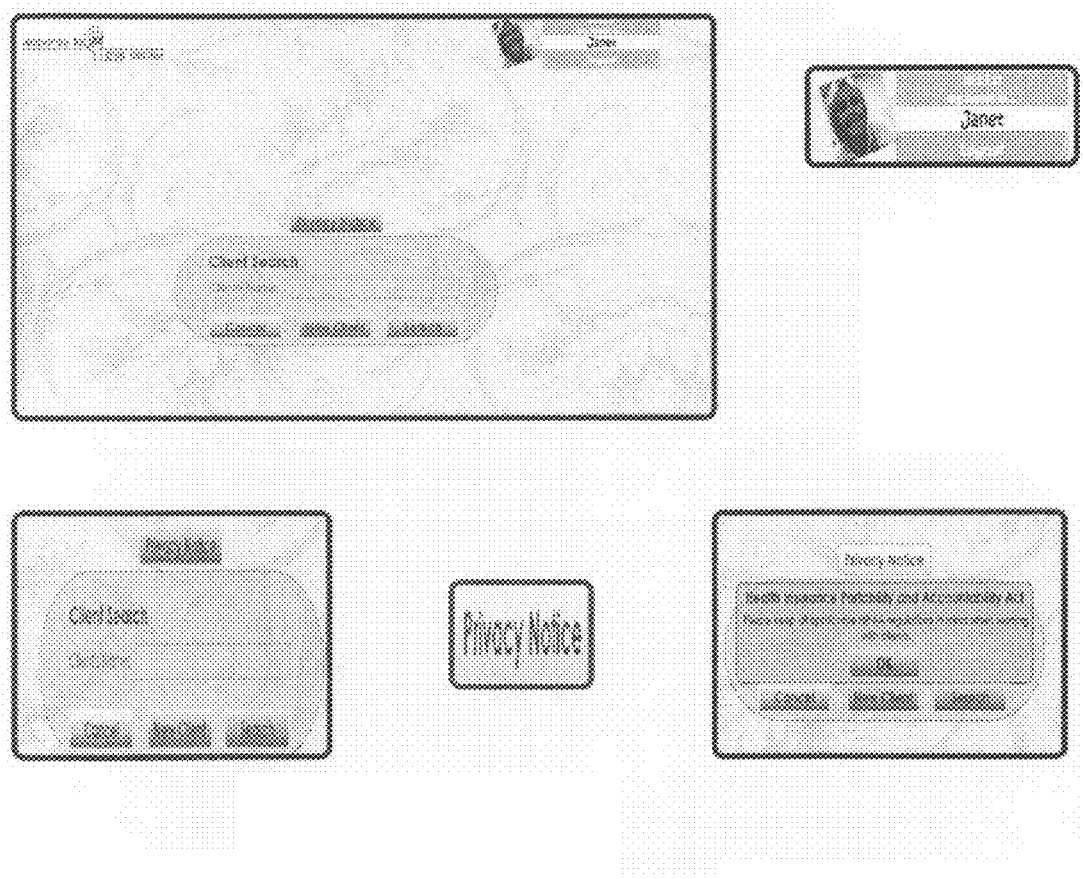

FIG. 3 includes one or more screen captures from a present invention system, hereinafter referred to as "the system," illustrating a procedure for entering a new patient in the system. This screen enables a user of the system, hereafter referred to as the "health coach," to start the process of entering a new client into the system and to show the client the Privacy Notice. In this scenario, Joseph, a new client, visits for the first time a clinic using the system. Janet, the health coach in this illustration, is able to review the Privacy Notice with Joseph. Janet's name and picture will appear on every page to reaffirm that she is legitimate. This allows Joseph to feel like he is in a secured environment. In subsequent screens (not shown) accessible from the screen in FIG. 3, information, such as background data 116 is gathered for Joseph. In the descriptions that follow, Janet and Joseph are used as examples of a patient and health coach/health care provider, respectively.

Figure 4:
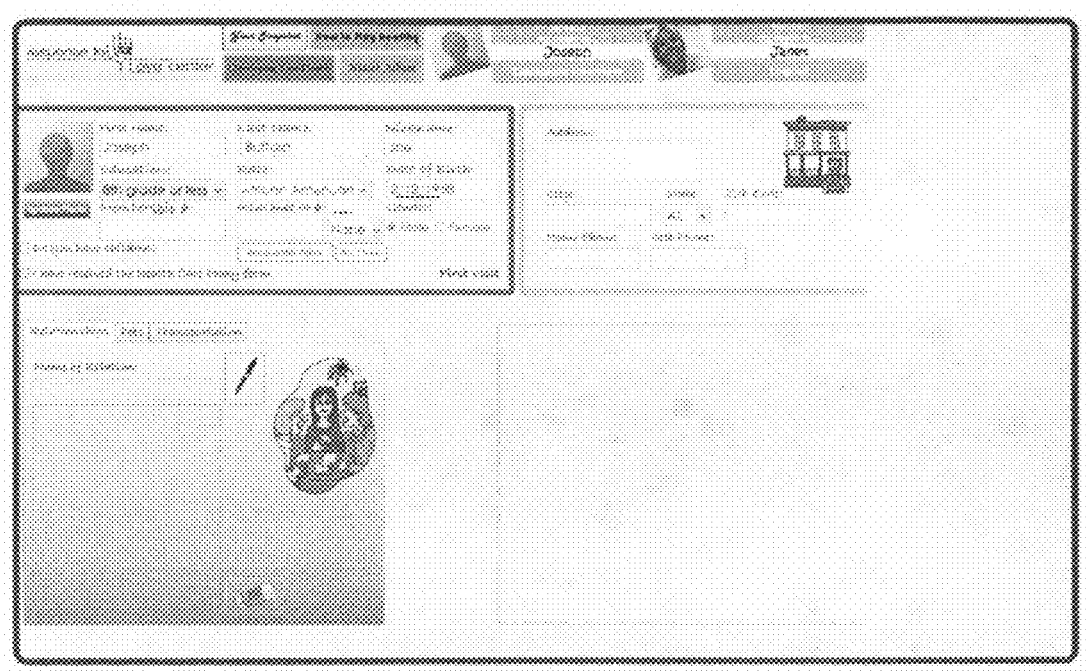

FIG. 4 includes one or more screen captures from the system illustrating a procedure for gathering and entering further data regarding a new patient. For example, Joseph has come to the clinic for the first time and Janet is obtaining and entering information, such as background data 116 for Joseph. A photograph of Joseph appears on the screen. In subsequent screens (not shown) accessible from the screen in FIG. 4, information, such as demographics, insurance coverage, health care proxy, emergency contacts, and pets is gathered for Joseph.

Figure 5:
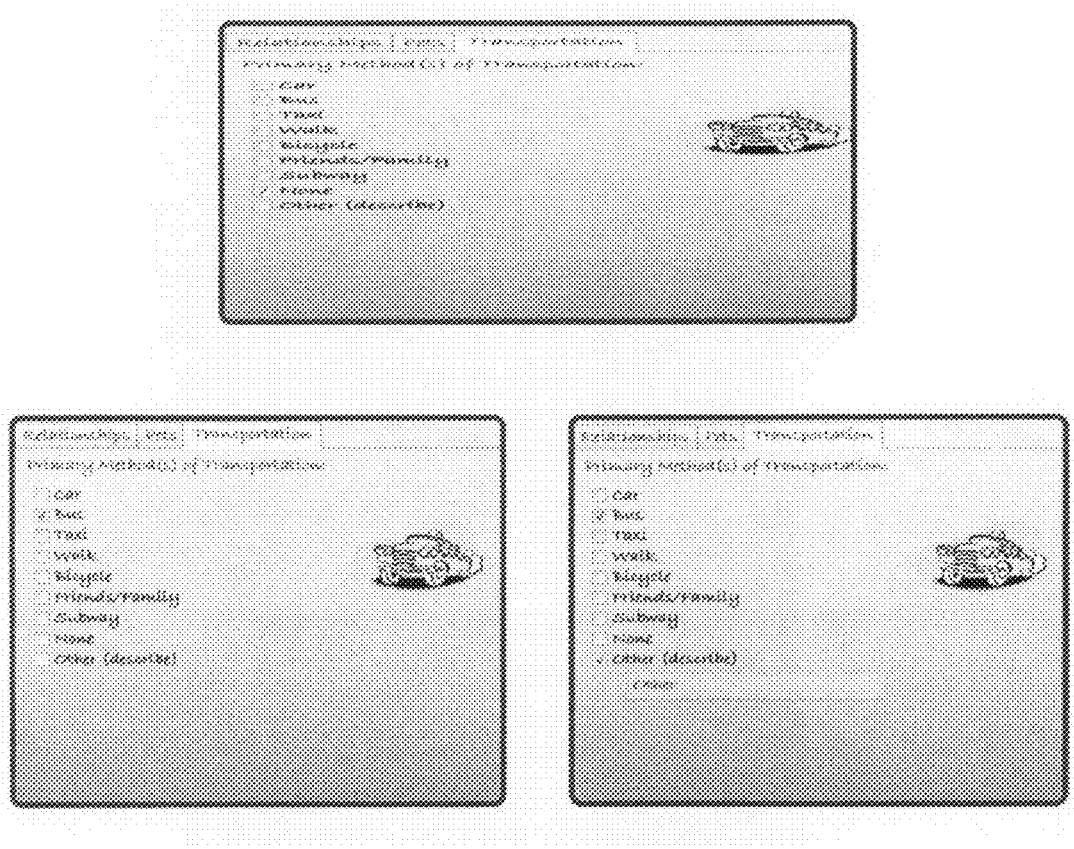

FIG. 5 includes one or more screen captures from the system illustrating a procedure for gathering and entering data, for example, data 110, regarding living conditions, or environmental conditions, for example, conditions 112, for a new patient. For example, the data is regarding the types of transportation to which Joseph has access. Thus, this screen enables the coach to gather data regarding aspects of the patient's living arrangement that present a concern for the patient and may impact the physical, mental, or emotional health of the patient.

Figure 6:
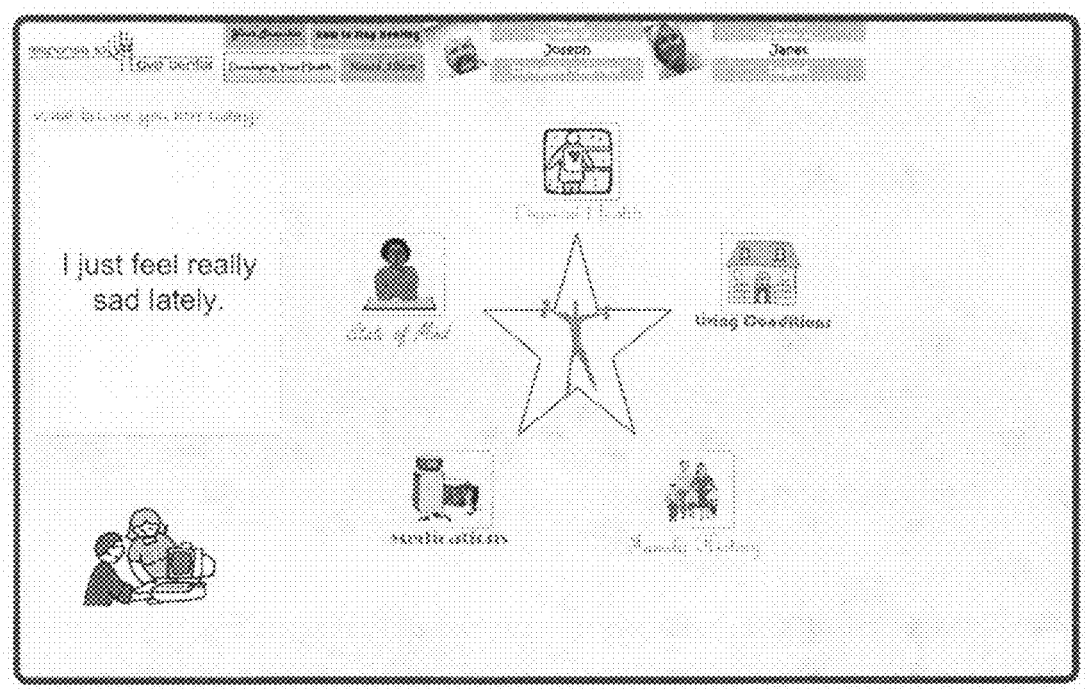

FIG. 6 includes one or more screen captures from the system illustrating a procedure for gathering and entering data regarding the purpose of a patient's visit. Pictorially represented options and aspects, in the form of icons, include 'Living Conditions,' 'State of Mind, 'Physical Health,' 'Family History,' and Medications.' In the scenario shown, Joseph has clicked on 'State of Mind' icon and told Janet that he is feeling sad lately.

Figure 7:
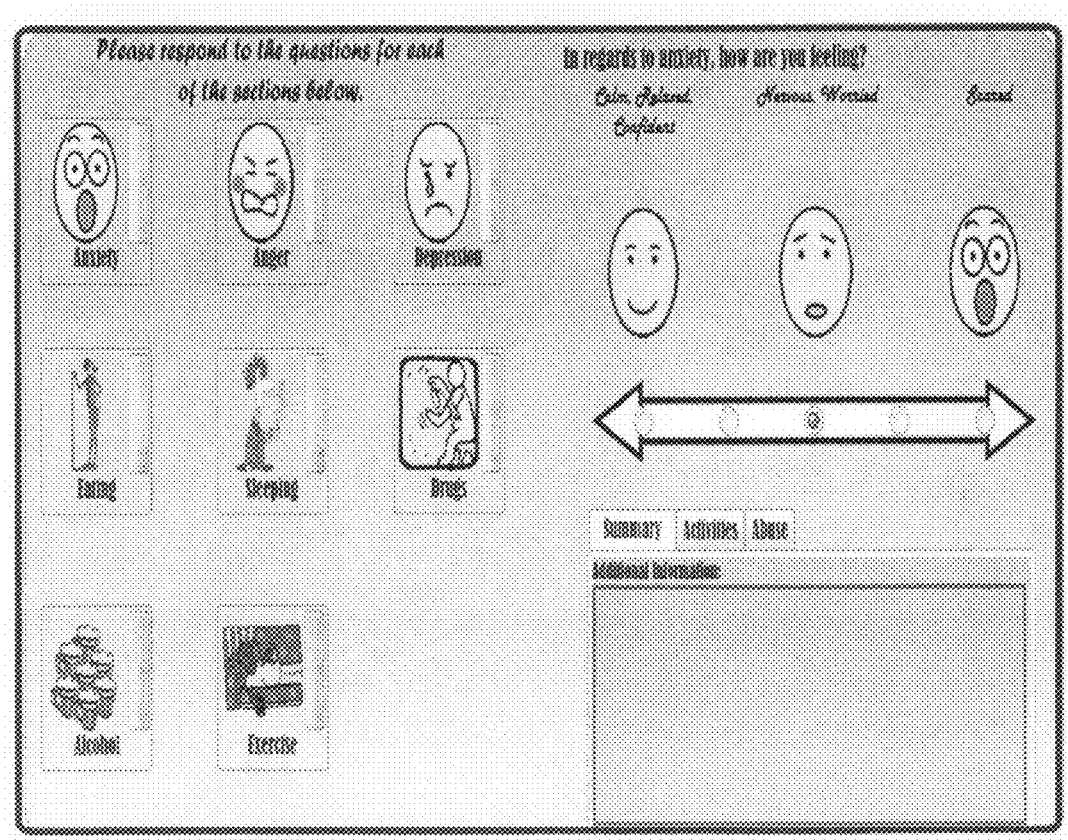

FIG. 7 includes one or more screen captures from the system illustrating a procedure for gathering and entering further data with respect to the 'State of Mind' option in FIG. 6. Using this screen, the health coach is able to gather further information regarding the patient's mental and emotional health. The screen has pictorial representations of various mood/emotions that the patient can select. For example, Joseph selects the icon for 'Anxiety.' In response to the selection of this icon an appropriate icon for gauging the intensity of the mood is displayed to the right. For example, in FIG. 7, faces illustrating levels of anxiety from 'calm' to 'scared' and a bar for choosing a level of intensity are displayed. Joseph has selected a level in the approximate mid-range of the bar.

Figure 8:
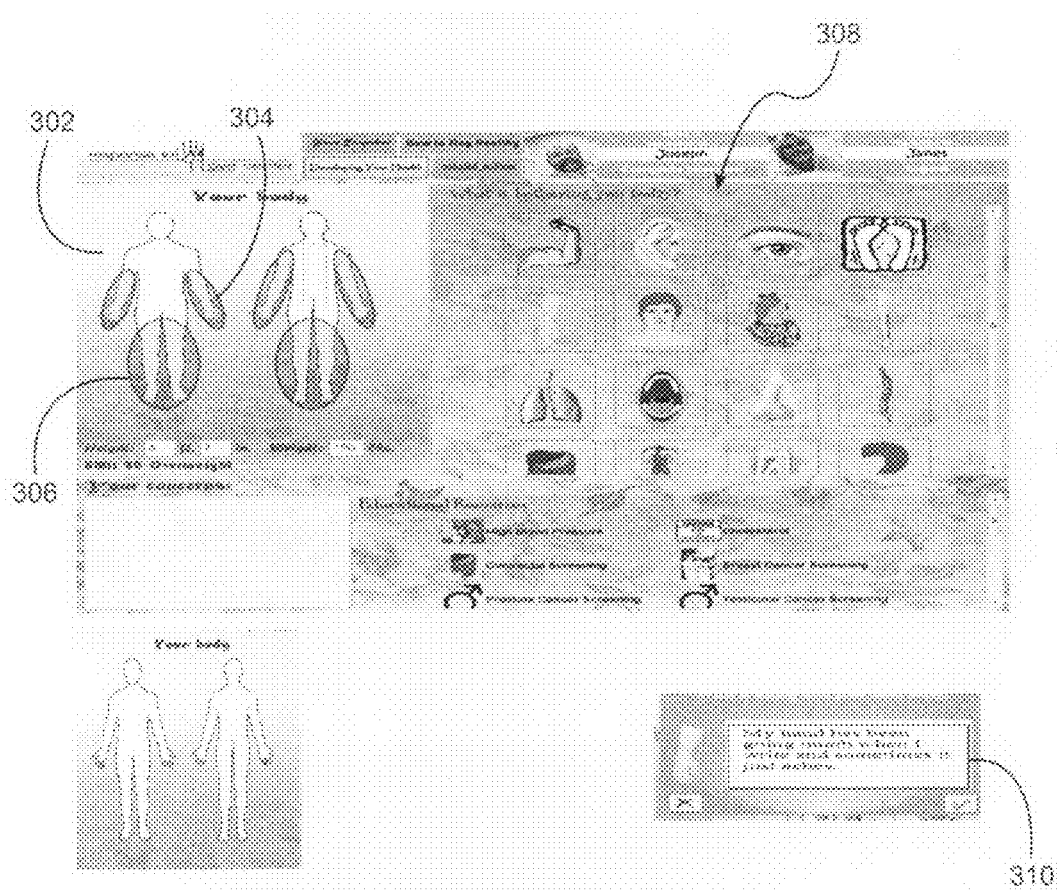

FIG. 8 includes one or more screen captures from the system illustrating a procedure for gathering and entering data regarding a patient's physical health and for generating and displaying applicable information. Janet returns to the screen in FIG. 6 and asks Joseph to click on the respective icon for another issue with which Joseph is concerned. Joseph selects the icon for 'Physical Health' to cause the screen in FIG. 8 to display. Thus, this interactive screen enables the client to select one or more physical complaints or concerns that they would like to discuss further with their health coach. The system gathers and enters this data, for example, as data 114. When the mouse cursor is placed over pictorial representation 302 of the human body, areas specific to a region on the human body, for example, arm area 304 or leg area 306 are shaded. Once a region has been selected by the patient or the coach, a series of icons corresponding to the selected body part are displayed in field 308, for example, for further discussion and documentation. In this case, Joe complains that his hand is hurting him and Janet selected area 304, an area that closely resembles the area of Joe' concern. In addition, Joe or Janet type in field 310 information regarding the concern, for example: "My hand has been going numb when I write and sometimes it just aches."

Figure 9:
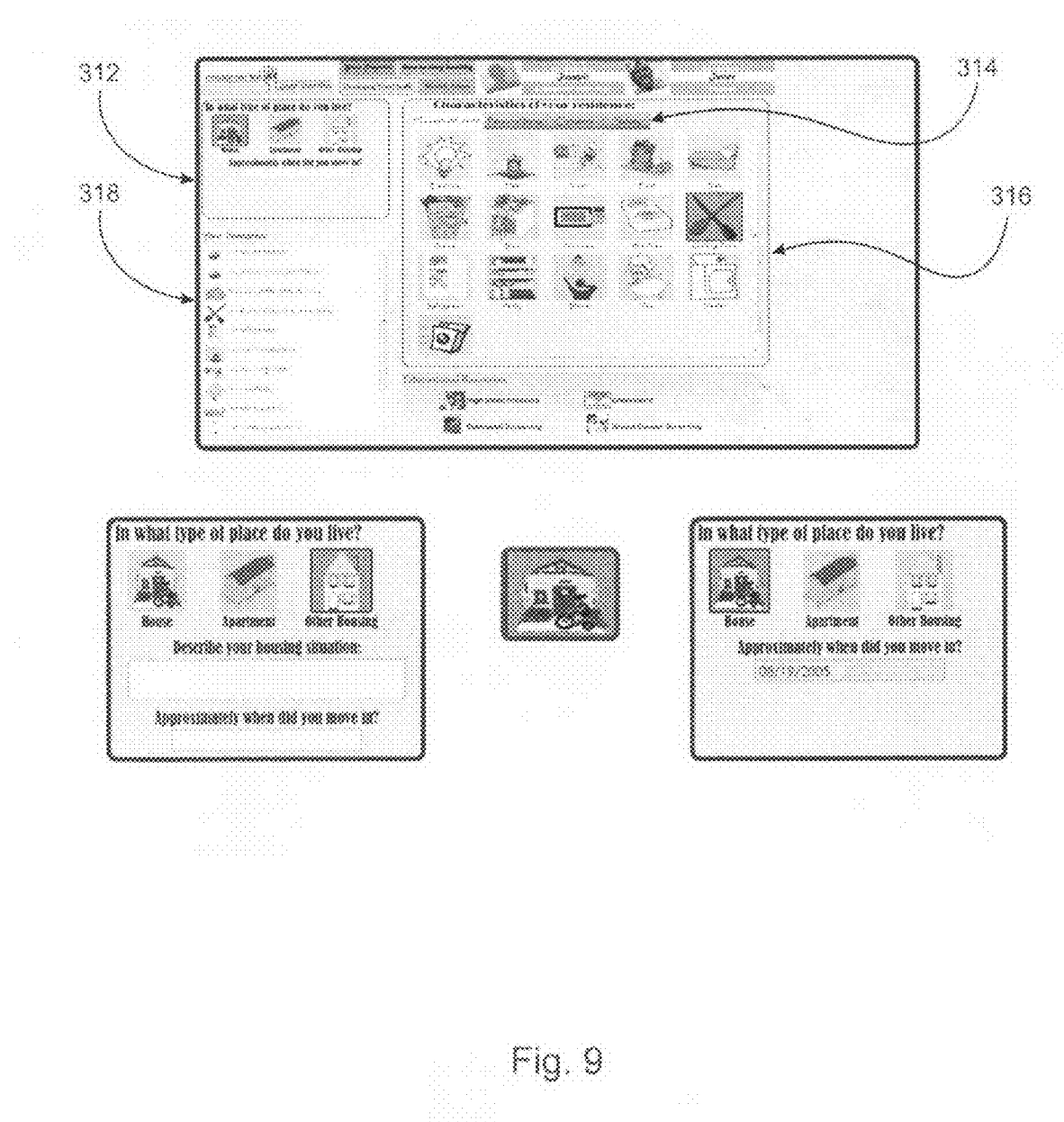

FIG. 9 includes one or more screen captures from the system illustrating a procedure for gathering and entering data regarding a patient's living conditions. Janet returns to the screen in FIG. 7 and asks Joseph to click on the respective icon for another issue with which Joseph is concerned. Joseph selects the icon for 'Living Conditions' to cause the screen in FIG. 9 to display. This screen enables the coach to gather information, for example, information 110, regarding the patient's environment, or living, conditions, for example, conditions 112. Field 312 pictorially represents possible types of housing that Joseph can view and select. If Joseph is homeless, this information is gathered and entered at this point. Tabs 314 are for general categories of characteristics for a residence. Field 316 is populated with icons according to the tab 314 selected. The tab for 'Household Items' is selected in FIG. 9 to generate the icons shown in field 316 in FIG. 9.

Figure 10:
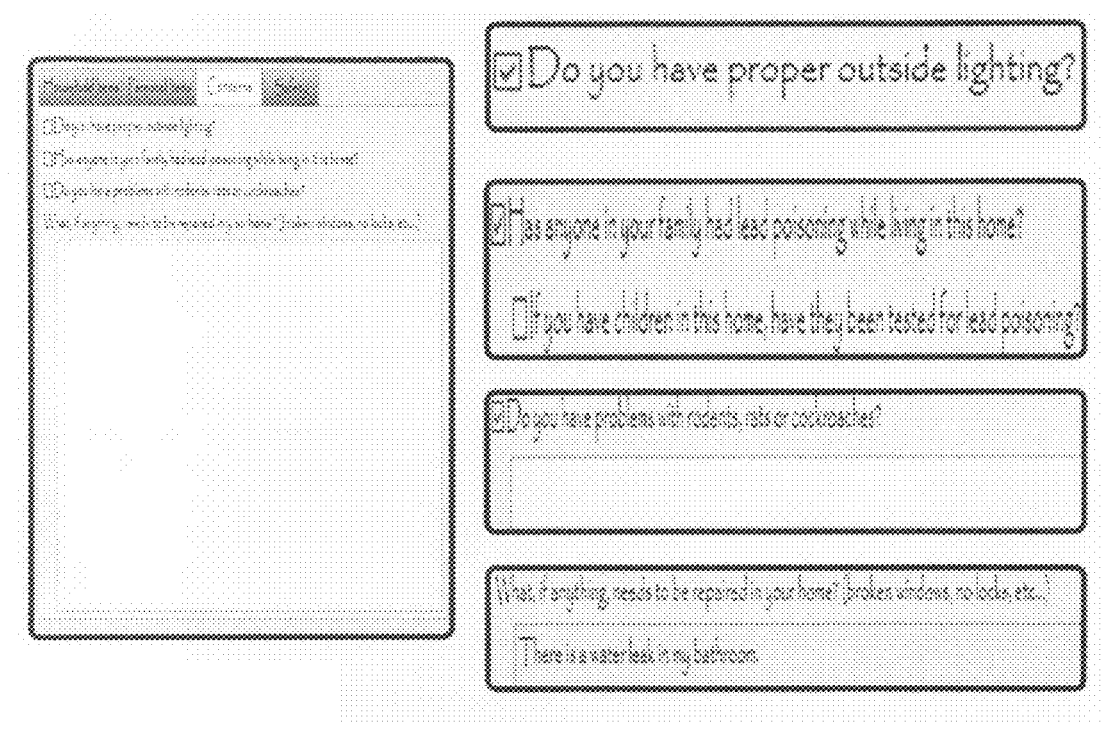

FIG. 10 includes one or more screen captures from the system illustrating a procedure for gathering and entering data regarding a patient's living conditions. To generate the screen shown in FIG. 10, the tab for 'Concerns' in FIG. 9 is selected. Field 316 is populated with a series of questions and a section for entering information regarding needed repairs or other miscellaneous items. For example, concerns not listed in field 316 can be entered in this section. The respective boxes are checked for questions in field 316 that represent concerns for the patient. For example, the patient selected boxes for outside lighting, lead poisoning, and rodents and a notation regarding a water leak is made. The items associated with the checked boxes, and the notation regarding the leak, are added to a concerns list, in field 318 in FIG. 9. Thus, this screen enables the coach to gather data regarding aspects of the patient's living arrangement that present a concern for the patient and may impact the physical, mental, or emotional health of the patient. The tab for 'Safety' is selected from tabs 314 to generate the screen in the next figure.

Figure 11:
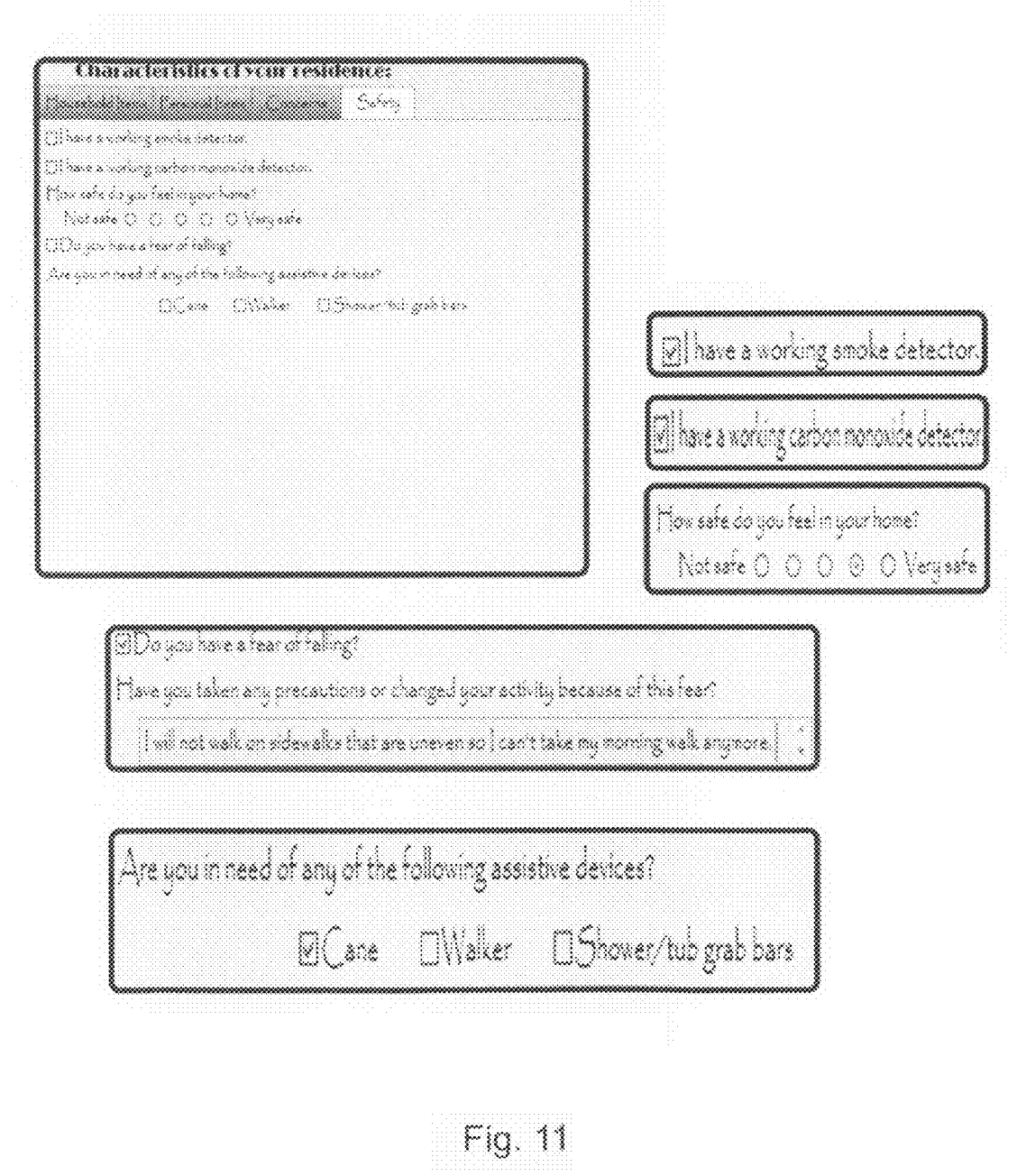

FIG. 11 includes one or more screen captures from the system illustrating a procedure for gathering and entering data regarding a patient's living conditions. Field 316 is populated with a series of questions regarding potential safety issues. The respective boxes are checked for questions in field 316 that represent safety concerns for the patient. For example, boxes for a smoke detector and carbon monoxide detector are checked and a perceived safety level is selected. The items associated with the checked boxes and the perceived safety level are added to the concerns list in field 318. Thus, this screen enables the coach to gather data regarding safety concerns for the patient that may impact the physical, mental, or emotional health of the patient. The tab for 'Household Items' is selected from tabs 314 to generate the screen in the next figure.

Figure 12:
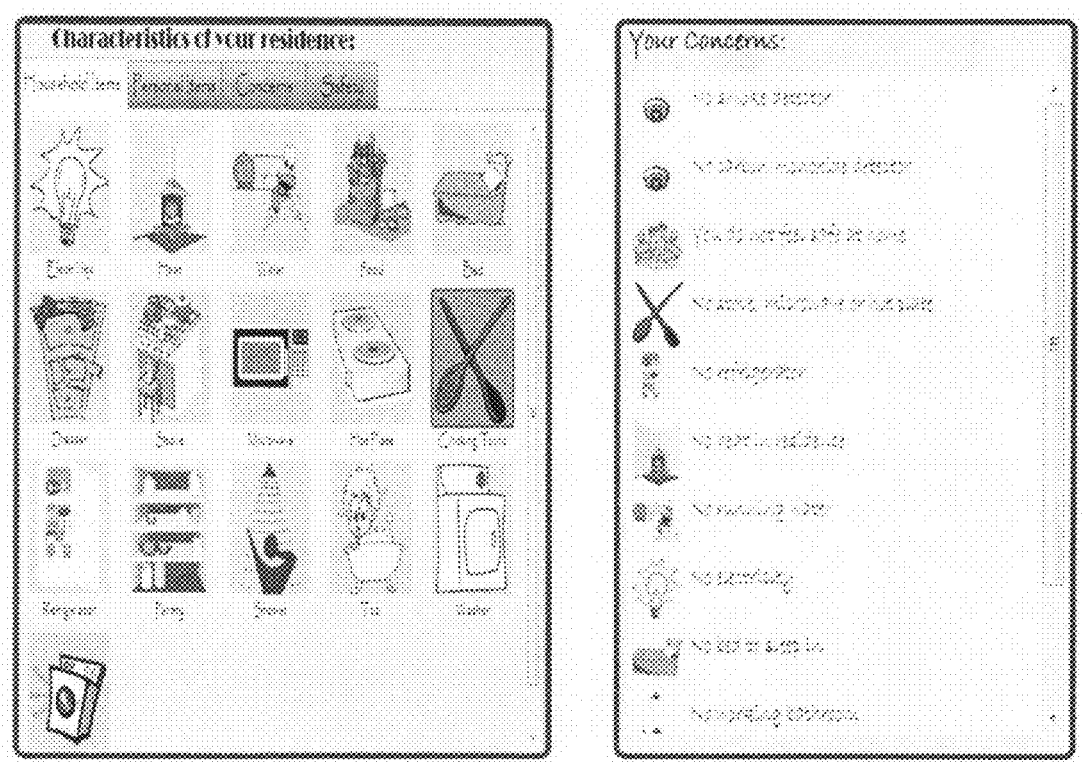

FIG. 12 includes one or more screen captures from the system illustrating a procedure for gathering and entering data regarding a patient's living conditions. Field 316 is populated with a series of icons regarding household items. Respective icons are selected that represent household items that the patient does not have (that are a concern). For example, boxes for cooking tools, heat, electricity, and a refrigerator are checked. The items associated with the selected icons are added to the concerns list in field 318. Thus, this screen enables the coach to gather data regarding household items that are lacking for the patient, present a concern for the patient and may impact the physical, mental, or emotional health of the patient. The tab for 'Personal Items' is selected from tabs 314 to generate the screen in the next figure.

Figure 13:
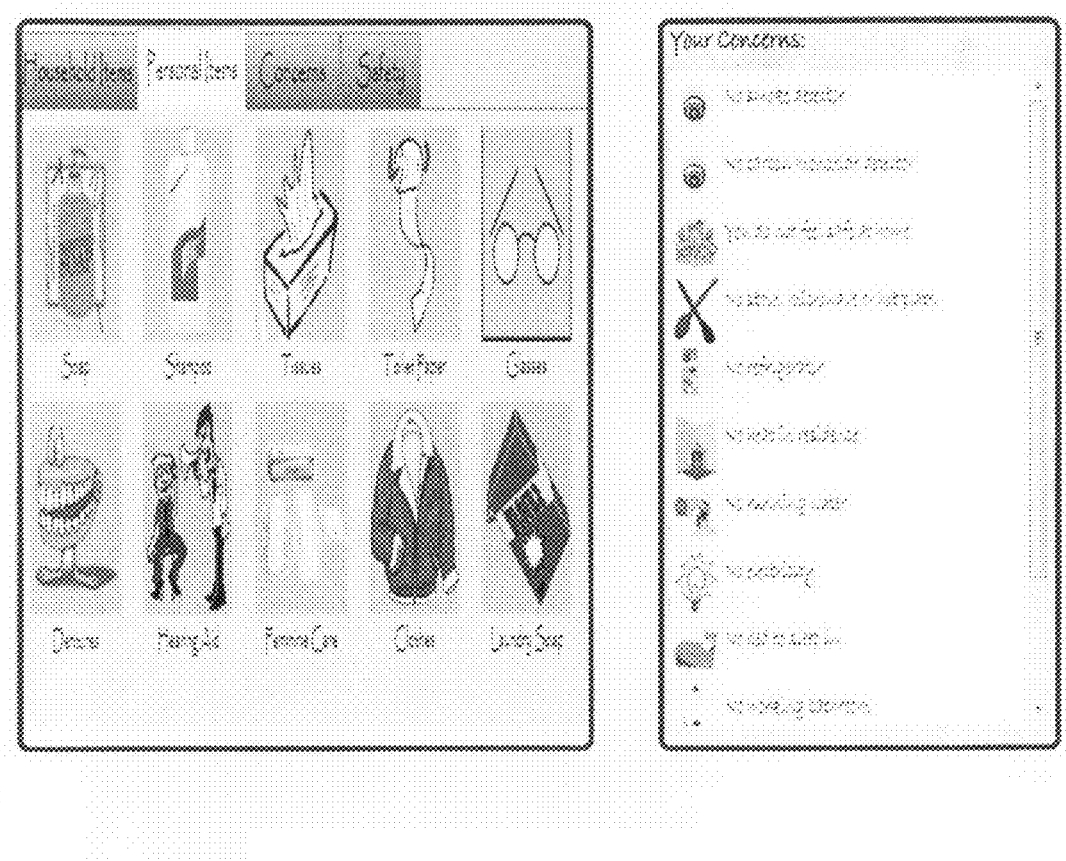

FIG. 13 includes one or more screen captures from the system illustrating a procedure for gathering and entering data regarding a patient's living conditions. Field 316 is populated with a series of icons regarding personal items. Respective icons are selected that represent personal items that the patient does not have (that are a concern). The items associated with the selected icons are added to the concerns list in field 318. Thus, this screen enables the coach to gather data regarding personal items that are lacking for the patient, present a concern for the patient and may impact the physical, mental, or emotional health of the patient. The icon for 'Colorectal Screening' is selected from the icons for 'Education Resources' in FIG. 9 to generate the screen in the next figure.

In one embodiment, in all or some of FIGS. 9-13: some or all of the screens shown are presentation 144, some or all of the inquiries are inquiries 146, and all or some of the conditions displayed are conditions 150.

Figure 14:
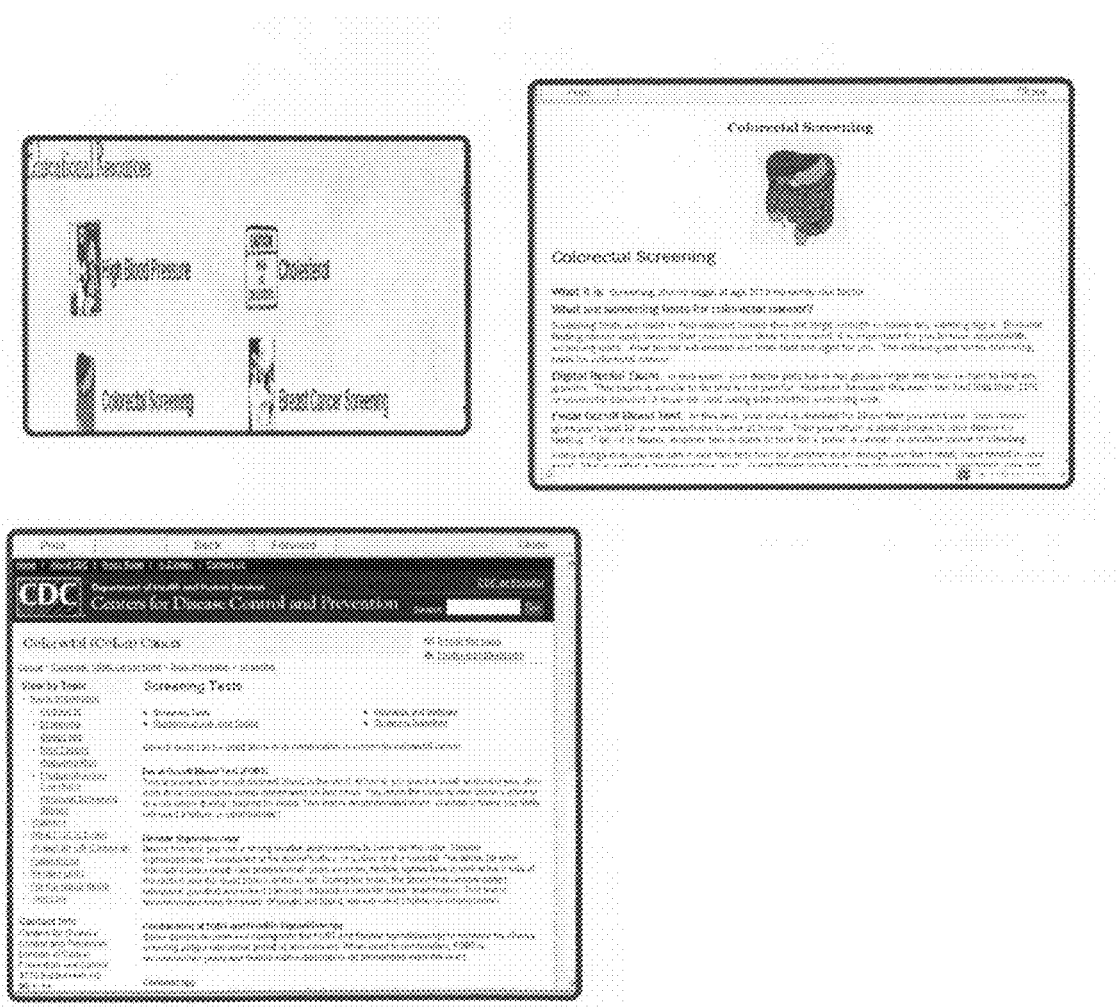

FIG. 14 includes one or more screen captures from the system illustrating a procedure for addressing concerns a patient may have. Information regarding colorectal screening is displayed in fields 316. For example, basic information regarding the screening and a website with more detailed information are presented.

Figure 15:
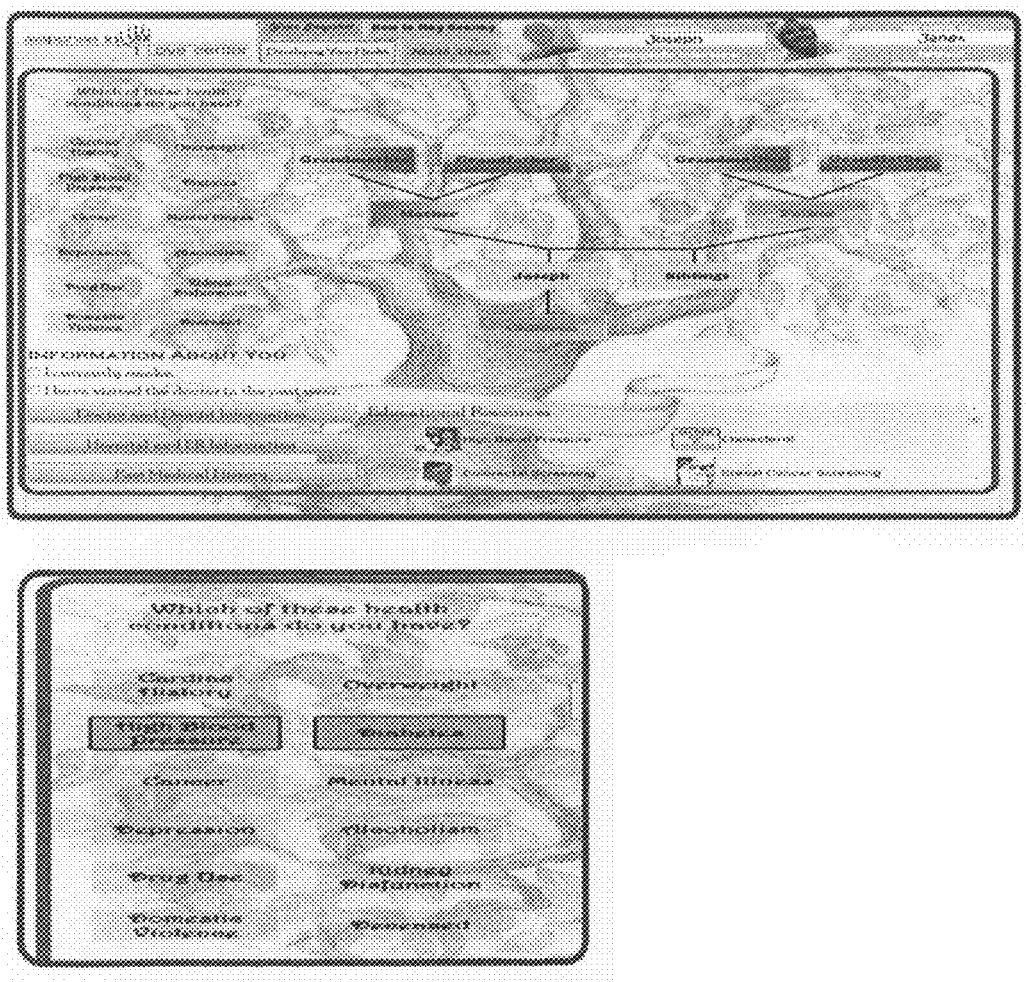

FIG. 15 includes one or more screen captures from the system illustrating a procedure for gathering and entering data regarding a patient's family history. Janet returns to the screen in FIG. 6 and selects the icon for 'Family History' to cause the screen in FIG. 15 to display. FIG. 15 is a pictorial representation of a possible family tree. This screen enables the coach to gather information regarding the patient's overall health conditions including access to health care and family medical history. For example, Joseph tells Janet that he has high blood pressure and diabetes and Janet selects corresponding icons accordingly. Icons also are displayed for obtaining the following for the patient: doctor and dentist information, hospital and emergency room information, and past medical history. When an icon for a member of the family tree is selected, for example, 'Mother,' icons related to possible health conditions, such as 'High Blood Pressure,' displayed to the left of the screen, can be selected to record health conditions associated with the selected member of the family tree. Note that the 'Educational Resources' icons, shown in FIG. 9 and described in FIG. 14, also appear in this figure. In general, these icons are presented where appropriate through the system displays.

Figure 16:
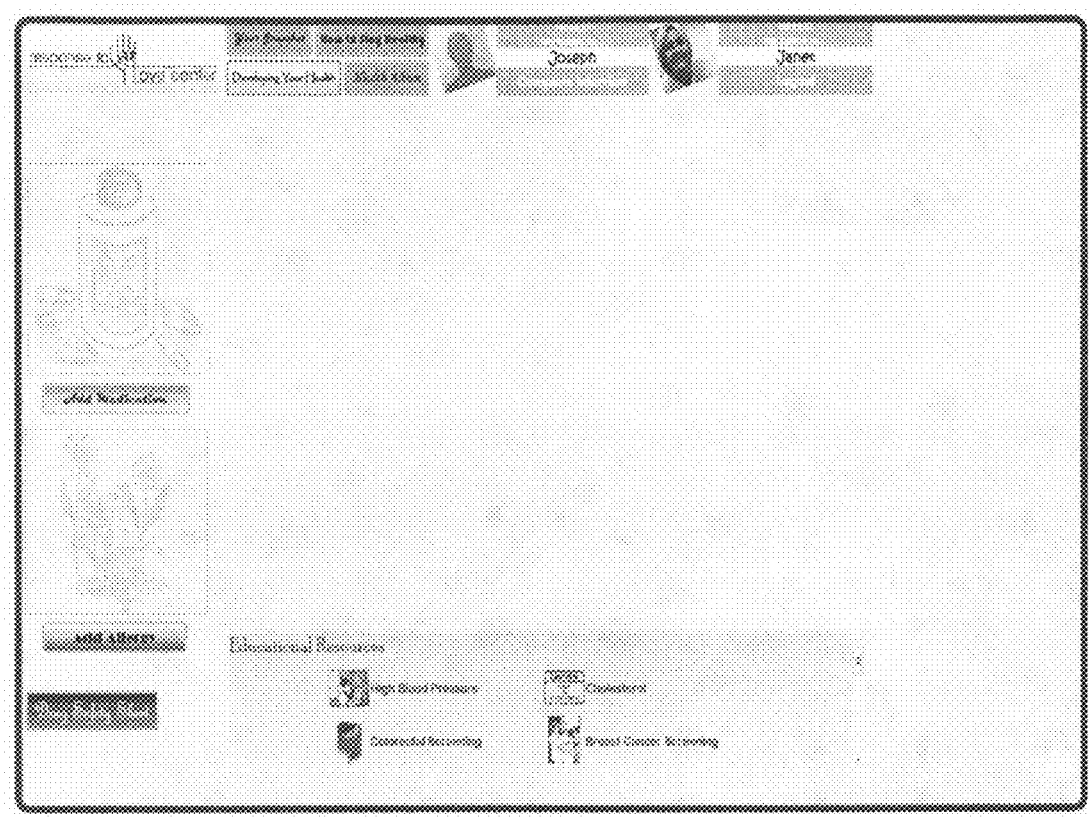

FIG. 16 includes one or more screen captures from the system illustrating a procedure for gathering and entering data regarding a patient's medications. Janet returns to the screen in FIG. 6 and selects the icon for 'Medications' to cause the screen in FIG. 16 to display. This screen enables the coach to gather information regarding the patient's medications and allergies. An icon for displaying drug safety information also is displayed. The 'Educational Resources' icons, shown in FIG. 9 also appear in this figure.

Figure 17:
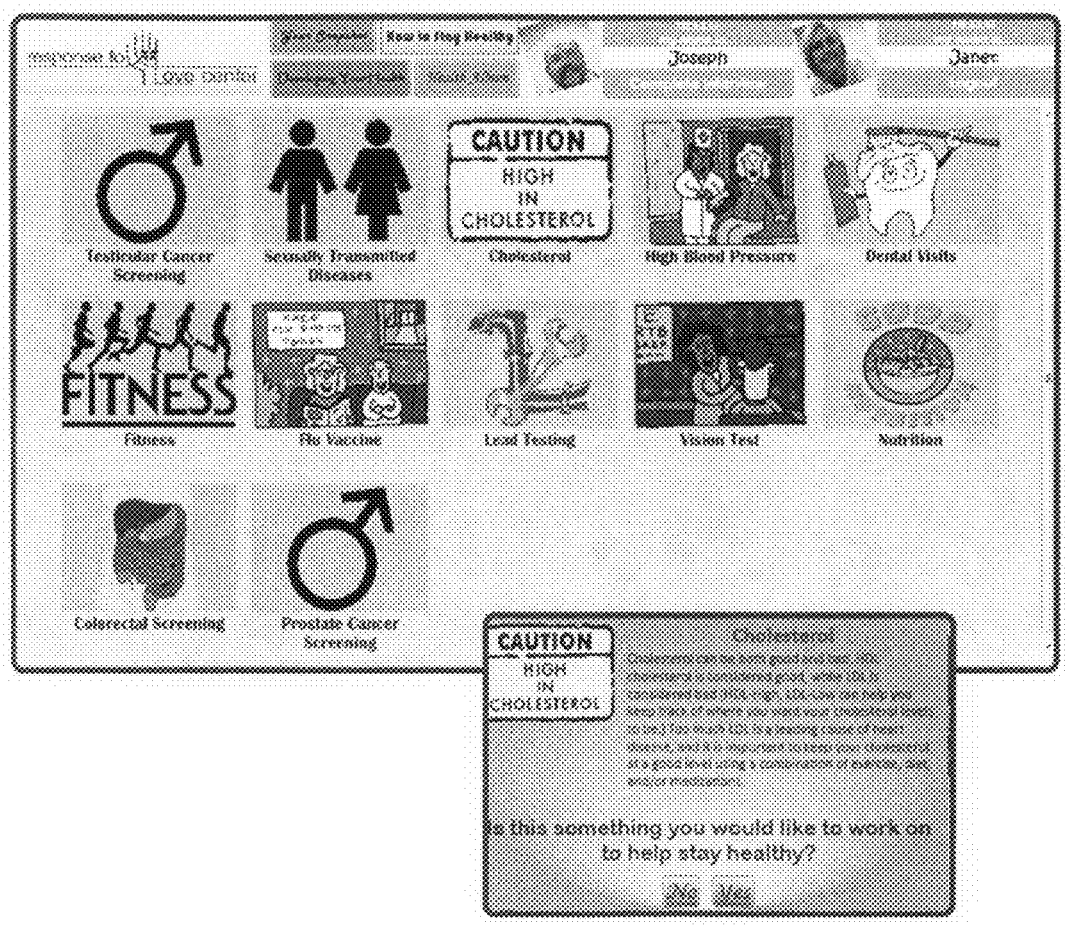

FIG. 17 includes one or more screen captures from the system illustrating a procedure for assessing a patient's understanding of preventative care. Janet returns to the screen in FIG. 6 and selects the tab for 'How to Stay Healthy' to cause the screen in FIG. 17 to display. As Joseph views the screen in FIG. 17, Janet asks Joseph which subjects he is concerned with or wishes to receive more information about. For example, Joseph expresses an interest in cholesterol and Janet selects the cholesterol icon to display further information regarding the subject.

Figure 18:
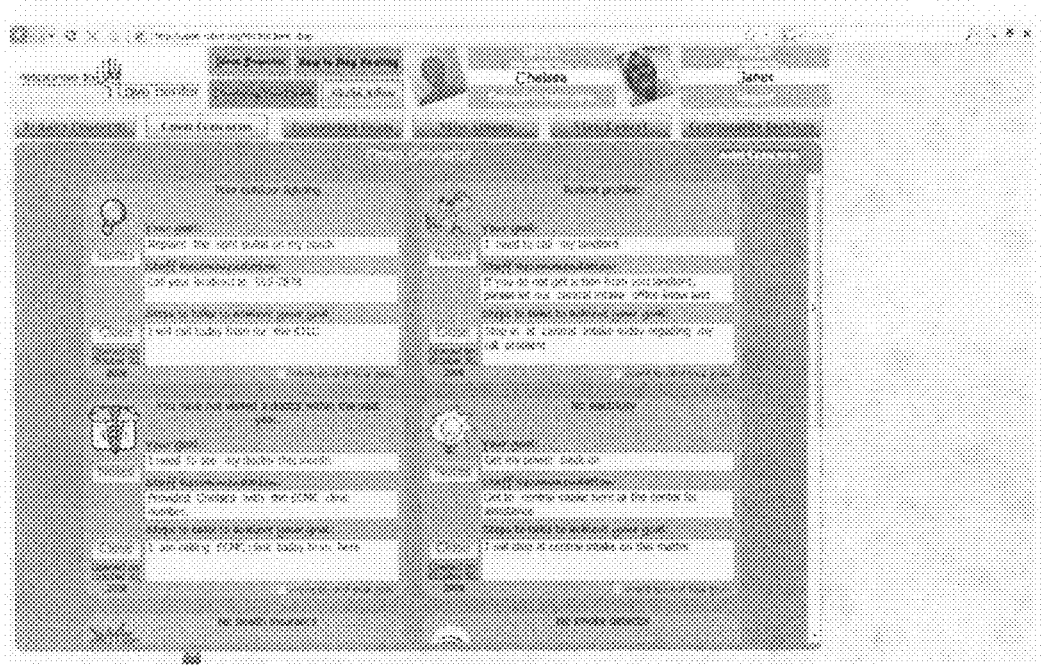
Figure 19:
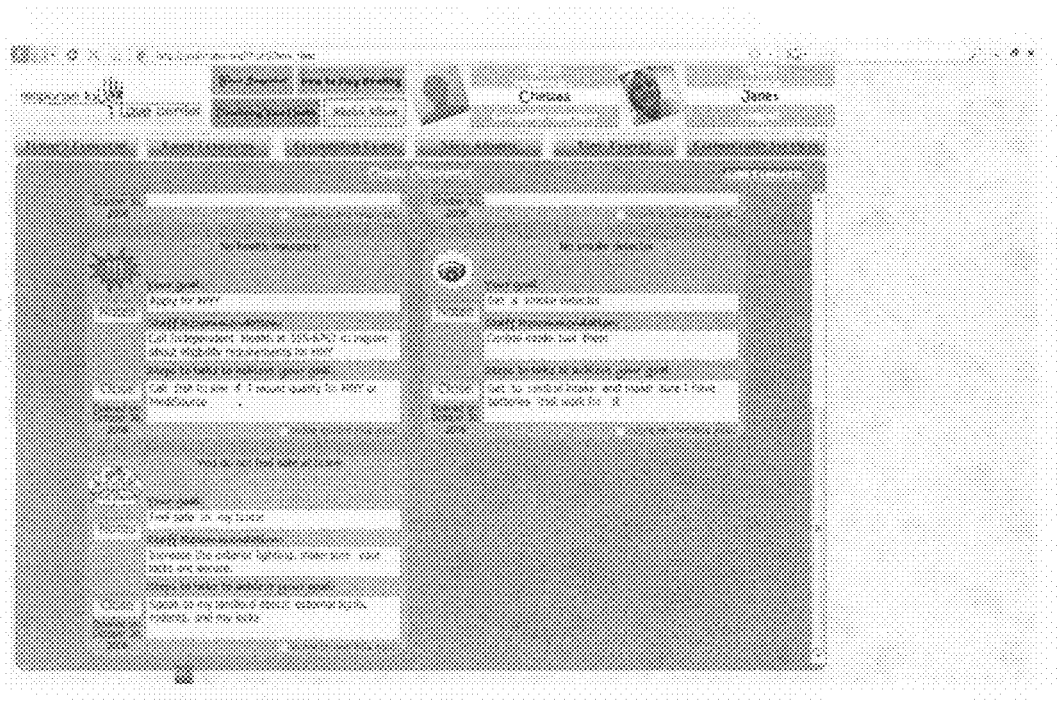

FIGS. 18 and 19 are screen captures from the system illustrating a procedure for summarizing a patient's visit. FIG. 18 shows the top portion of a display and FIG. 19 shows the screen in FIG. 18 scrolled down to show the rest of the display. Note that the name of the patient has changed in FIG. 18. Janet and the patient, Chelsea, have gone through a process as described supra to gather data and identify concerns related to Chelsea. For example, from the screen shown in FIG. 6, Janet selects the icon for 'Health Album' to cause the screen in FIG. 18 to display. The screen displays the concerns identified with respect to the patient, recommendations for addressing the concerns, and steps to implement the recommendations. In FIG. 18, concerns associated with the patient's physical health (have not visited a doctor within the past year) and environmental, or living, conditions are shown. Thus, in addition to addressing the physical health or symptoms of the patient, environment or living conditions that could affect the physical, mental, or emotional health and well being of the patient are advantageously included. For example, the patient has identified problems with a porch light, smoke detector, and electrical service. In one embodiment, the recommendations and steps for implementation are inputted by the user of system 100, for example, the health care provider. In one embodiment, system 100 automatically generates and displays recommendations and steps. In one embodiment, the recommendations or steps are produced by a combination of user input and automatic generation.

Figure 20:
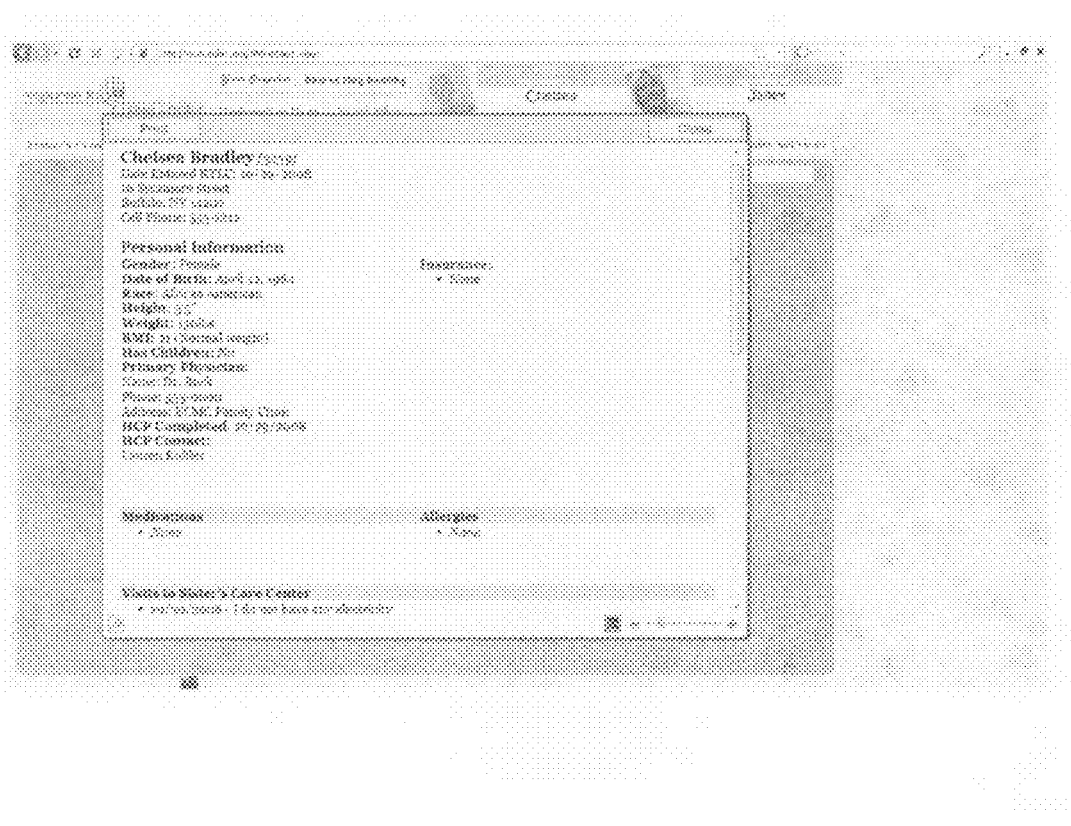
Figure 21:
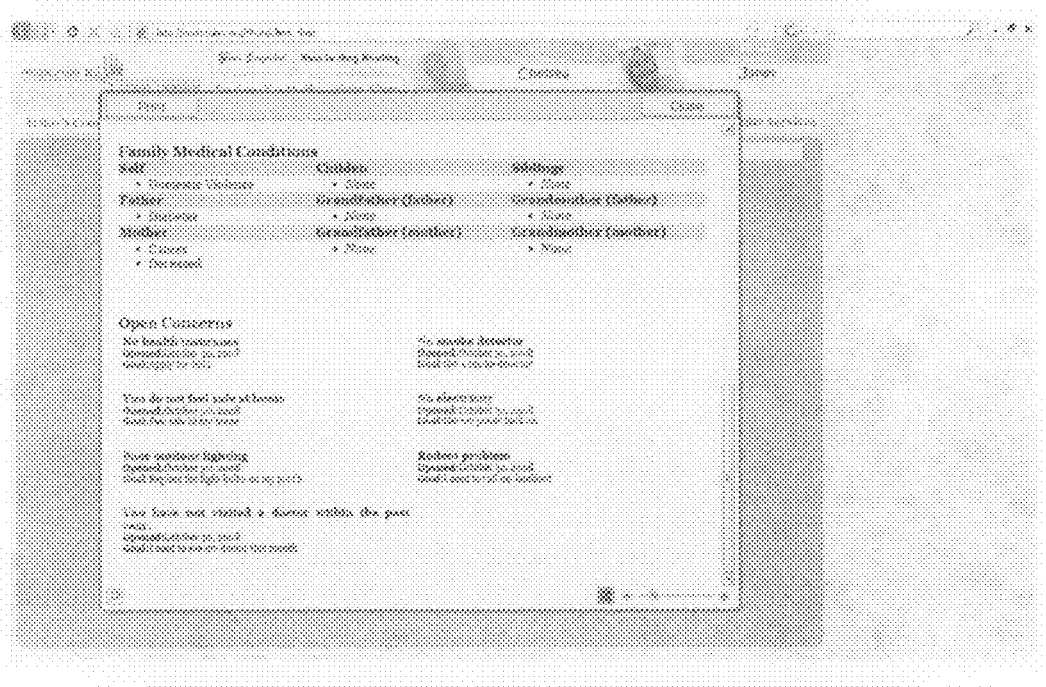

FIGS. 20 and 21 are screen captures from the system illustrating a procedure for summarizing a patient's visit. FIG. 20 shows the top portion of a display and FIG. 21 shows the screen in FIG. 20 scrolled down to show the rest of the display. Janet has selected the print option to display a printable summary of the information shown in FIGS. 18 and 19. This summary shows that a full range of factors regarding the physical, mental, or emotional health and well being of the patient have been identified and addressed. For example, the patient's family history is shown as well as the open concerns shown in FIGS. 18 and 19.

Thus, it is seen that the objects of the invention are efficiently obtained, although changes and modifications to the invention should be readily apparent to those having ordinary skill in the art, without departing from the spirit or scope of the invention as claimed. Although the invention is described by reference to a specific preferred embodiment, it is clear that variations can be made without departing from the scope or spirit of the invention as claimed.

What is claimed is:

1. A method for managing electronic health records, comprising:

receiving, using an interface element in at least one specially programmed general-purpose computer, first data regarding at least one environmental condition related to a patient, second data regarding at least one symptom of the patient related to physical or mental health of the patient, and background data for the patient;

storing the first, second, and background data in a memory element for the at least one specially programmed general-purpose computer;

generating, using a processor in the at least one specially programmed general-purpose computer and the first, second, and background data, information regarding at least one concern applicable to the physical or mental health of the patient;

generating, using the processor and the first, second, and background data, at least one action item for addressing the at least one concern;

storing, in the memory element, the at least one action item;

transmitting, using the interface element, at least a portion of the information regarding the at least one concern for the physical or mental health of the patient for display and the at least one action item for display;

receiving, using the interface element, third data regarding compliance with the at least one action item, the third data including information as to whether the at least one action item has been complied with; and, when the at least one action item has not been complied with, transmitting, using the interface element, the at least one action item for display; or, when the at least one action item has been complied with, modifying the stored at least one action item to indicate that the at least one action has been complied with; and, transmitting for display, using the interface element, a message that the at least one action item has been complied with, wherein the at least one environmental condition is selected from the group consisting of conditions in the vicinity of the patient's residence, utilities for and infrastructure of the patient's residence, household items associated with the patient's residence, personal items belonging to the patient, transportation options available to the patient, and the patient's perceived level of safety in their residence.

2. The method of claim 1 wherein the at least one action item includes an action item directed to an environmental condition from the at least one environmental condition, the method further comprising:
generating, using the processor, a graphical presentation including at least one inquiry, in the form of a pictorial display, regarding compliance of the patient with the action item directed to an environmental condition; and,
transmitting, using the interface element, the graphical presentation for display on a graphical user interface (GUI), wherein receiving the third data includes receiving data regarding compliance of the patient with the action item directed to an environmental condition via a GUI on which the graphical presentation is displayed.

3. The method of claim 1 further comprising:
generating, using the processor, a graphical presentation including a plurality of inquiries, in the form of respective pictorial displays, regarding a plurality of respective environmental conditions; and,
transmitting, using the interface element, the graphical presentation for display on a GUI, wherein receiving the first data includes receiving at least a portion of the first data via a GUI on which the graphical presentation is displayed.

4. The method of claim 1 wherein the at least one action item addresses an environmental condition from the at least one environmental condition.

5. The method of claim 1 further comprising:
generating, using the processor, an inquiry as to whether the patient wishes further information regarding the at least one health concern;
transmitting, using the interface element, the inquiry for display;
receiving, using the interface element, an affirmative response to the inquiry, including a request for further information regarding a health concern from the at least one health concern;
generating, using the processor, information regarding the health concern, the information regarding the health concern more detailed than the information regarding the at least one concern for the physical or mental health of the patient; and,
transmitting, using the interface element, the information regarding the health concern.

6. The method of claim 1 wherein the at least one action items includes a plurality of action items, the method further comprising when a first action item from the plurality of action items has not been complied with and when a second action item from the plurality of action items has been complied with:
transmitting, using the interface element, the first action item for display;
modifying the stored second action item to indicate that the second action has been complied with; and,
transmitting for display, using the interface element, a message that the second action item has been complied with.

7. A system for managing electronic health records, comprising:
a processor in at least one specially programmed general-purpose computer for generating a graphical presentation including at least one inquiry, in the form of a pictorial display, regarding at least one environmental conditions related to a patient;
an interface element in the at least one specially programmed general-purpose computer for:
transmitting the graphical presentation for display on a GUI; and,
receiving first data regarding at least one respective environmental condition, from the plurality of respective environmental conditions, related to the patient, second data regarding at least one symptom of the patient related to physical or mental health of the patient, and background data for the patient; and
a memory element for the at least one specially programmed general-purpose computer for storing the first, second, and background data, wherein the processor is for:
generating, using the first, second, and background data, information regarding at least one concern with respect to the physical or mental health of the patient; and,
generating, using the first, second, and background data, at least one action item for addressing the at least one concern, wherein the interface element is for transmitting at least a portion of the information regarding at least one concern for the physical or mental health of the patient and the at least one action item for display and receiving third data regarding compliance with the at least one action item, wherein the at least one environmental condition is selected from the group consisting of the type of residence in which the patient lives, conditions in the vicinity of the patient's residence, utilities for and infrastructure of the patient's residence, household items associated with the patient's residence, personal items belonging to the patient, transportation options available to the patient, and the patient's perceived level of safety in their residence.

8. The system of claim 7 wherein:
the at least one action item includes an action item directed to an environmental condition from the at least one environmental condition;
the processor is for generating a graphical presentation including at least one inquiry, in the form of a pictorial display, regarding compliance of the patient with the action item directed to an environmental condition; and,
the interface element is for transmitting the graphical presentation for display on a graphical user interface (GUI) and receiving data regarding compliance of the patient with the action item directed to an environmental condition via a GUI on which the graphical presentation is displayed.

9. The system of claim 7 wherein
the interface element is for receiving at least a portion of the first data via the GUI on which the graphical presentation is displayed.

10. The system of claim 7 wherein the at least one action item addresses an environmental condition from the at least one environmental condition.

11. The system of claim 7 wherein:
the processor is for generating an inquiry as to whether the patient wishes further information regarding the at least one health concern;

the interface element is for transmitting the inquiry for display and receiving an affirmative response to the inquiry, including a request for further information regarding a health concern from the at least one health concern;

the processor is for generating information regarding the health concern, the information regarding the health concern more detailed than the information regarding at least one concern for the physical or mental health of the patient; and, the interface element is for transmitting the information regarding the health concern.

12. A method for managing electronic health records, comprising:

receiving, using an interface element in at least one specially programmed general-purpose computer, first data regarding at least two environmental conditions related to a patient, second data regarding at least one symptom of the patient related to physical or mental health of the patient, and background data for the patient;

storing the first, second, and background data in a memory element for the at least one specially programmed general-purpose computer;

generating, using a processor in the at least one specially programmed general-purpose computer and the first, second, and background data, information regarding at least one concern applicable to the physical or mental health of the patient;

generating, using the processor and the first, second, and background data, at least one action item for addressing the at least one concern;

storing, in the memory element, the at least one action item;

transmitting, using the interface element, at least a portion of the information regarding the at least one concern for the physical or mental health of the patient for display and the at least one action item for display;

receiving, using the interface element, third data regarding compliance with the at least one action item, the third data including information as to whether the at least one action item has been complied with; and, when the at least one action item has not been complied with, transmitting, using the interface element, the at least one action item for display; or, when the at least one action item has been complied with, modifying the stored at least one action item to indicate that the at least one action has been complied with; and, transmitting for display, using the interface element, a message that the at least one action item has been complied with, wherein the at least two environmental conditions are selected from the group consisting of the type of residence in which the patient lives, conditions in the vicinity of the patient's residence, utilities for and infrastructure of the patient's residence, household items associated with the patient's residence, personal items belonging to the patient, transportation options available to the patient, and the patient's perceived level of safety in their residence.

\* \* \* \* \*